United States Patent
Jones et al.

(10) Patent No.: US 9,399,146 B2
(45) Date of Patent: Jul. 26, 2016

(54) METHODS OF TREATING ACNE USING DUAL PANEL PHOTODYNAMIC THERAPY LAMP

(71) Applicant: PHOTOCURE ASA, Oslo (NO)

(72) Inventors: Ross Peter Jones, Cambridge (GB); Michael John Cox, Herts (GB); Euan Morrison, Cambridge (GB)

(73) Assignee: Photocure ASA, Oslo (NO)

( * ) Notice: Subject to any disclaimer, the term of this patent is extended or adjusted under 35 U.S.C. 154(b) by 0 days.

(21) Appl. No.: 14/863,987

(22) Filed: Sep. 24, 2015

(65) Prior Publication Data

US 2016/0008623 A1 Jan. 14, 2016

Related U.S. Application Data

(63) Continuation of application No. 13/646,274, filed on Oct. 5, 2012.

(30) Foreign Application Priority Data

Aug. 30, 2012 (EP) .................................. 12182486

(51) Int. Cl.
*A61N 5/06* (2006.01)

(52) U.S. Cl.
CPC .............. *A61N 5/062* (2013.01); *A61N 5/0616* (2013.01); *A61N 2005/0633* (2013.01); *A61N 2005/0642* (2013.01); *A61N 2005/0652* (2013.01); *A61N 2005/0663* (2013.01)

(58) Field of Classification Search
CPC ... A61N 5/062; A61N 5/0614; A61N 5/0616; A61N 2005/0652; A61N 2005/0653; A61B 2018/00452

See application file for complete search history.

(56) References Cited

U.S. PATENT DOCUMENTS

| | | | |
|---|---|---|---|
| 5,634,711 | A | 6/1997 | Kennedy et al. |
| 6,558,411 | B1 | 5/2003 | Steen |
| 6,872,220 | B2 | 3/2005 | Williams et al. |
| 7,077,544 | B2 | 7/2006 | Parker |
| 7,207,694 | B1 | 4/2007 | Petrick |
| 7,311,722 | B2 | 12/2007 | Larsen |
| 7,517,101 | B2 | 4/2009 | Tobin |

(Continued)

FOREIGN PATENT DOCUMENTS

| | | |
|---|---|---|
| WO | 96-28412 A1 | 9/1996 |
| WO | 99/53962 A1 | 10/1999 |

(Continued)

OTHER PUBLICATIONS

Bissonnette MD, Robert, et al., "Photodynamic Therapy With Methylaminolevulinate 80 mg/g Without Occlusion Improves Acne Vulgaris", Journal of Drugs in Dermatology, Nov. 2010, vol. 9, Issue 11, pp. 1347-1352.

(Continued)

Primary Examiner — Lynsey Crandall
Assistant Examiner — Nathan J Jenness
(74) Attorney, Agent, or Firm — Kenyon & Kenyon LLP

(57) ABSTRACT

A photodynamic therapy lamp includes two lamp modules comprising an array of LEDs. Each of the lamp modules is movable between a first position in which an angle between the lamp modules is from 157 degrees to 180 degrees, and a second position in which the angle between the lamp modules is from 50 degrees to 70 degrees.

25 Claims, 13 Drawing Sheets

(56) References Cited

U.S. PATENT DOCUMENTS

| | | |
|---|---|---|
| 2002/0029071 A1 | 3/2002 | Whitehurst |
| 2003/0004499 A1 | 1/2003 | McDaniel |
| 2003/0023283 A1 | 1/2003 | McDaniel |
| 2003/0216795 A1 | 11/2003 | Harth et al. |
| 2004/0260365 A1 | 12/2004 | Groseth et al. |
| 2005/0090877 A1 | 4/2005 | Harth et al. |
| 2005/0124984 A1 | 6/2005 | Wagnieres et al. |
| 2006/0129209 A1 | 6/2006 | McDaniel |
| 2006/0200213 A1 | 9/2006 | McDaniel |
| 2006/0229689 A1 | 10/2006 | Ferguson et al. |
| 2006/0293727 A1 | 12/2006 | Spooner et al. |
| 2007/0197884 A1 | 8/2007 | Bornstein |
| 2007/0283655 A1* | 12/2007 | Tobin ............... A61N 5/0616 52/478 |
| 2008/0064752 A1 | 3/2008 | Braenden et al. |
| 2008/0091250 A1 | 4/2008 | Powell |
| 2008/0188558 A1 | 8/2008 | Godal et al. |
| 2010/0106228 A1 | 4/2010 | Gardner |
| 2010/0137439 A1 | 6/2010 | Wulf et al. |
| 2010/0174222 A1 | 7/2010 | McDaniel |
| 2010/0273725 A1 | 10/2010 | Glanzmann et al. |
| 2010/0331929 A1 | 12/2010 | Burrows et al. |
| 2011/0020441 A1 | 1/2011 | Klaveness et al. |
| 2011/0106222 A1 | 5/2011 | Wilson et al. |
| 2011/0212146 A1 | 9/2011 | Helland et al. |
| 2011/0293528 A1 | 12/2011 | Godal et al. |
| 2011/0295186 A1* | 12/2011 | Klem ............... A61N 5/0603 604/20 |
| 2012/0116484 A1 | 5/2012 | Bornstein |
| 2012/0136055 A1 | 5/2012 | Stensrud |
| 2012/0296260 A1 | 11/2012 | Vizethum et al. |

FOREIGN PATENT DOCUMENTS

| | | |
|---|---|---|
| WO | 02/098508 A1 | 12/2002 |
| WO | 2009/133385 A1 | 11/2009 |
| WO | 2010/142430 A1 | 12/2010 |
| WO | 2011/161220 A1 | 12/2011 |
| WO | 2012/004399 A1 | 1/2012 |

OTHER PUBLICATIONS

Photocure ASA e-mail press release dated Jan. 6, 2010, "Photocure ASA (se)—Photocure—Inclusion completed in phase II study in acne with Visonac (TM) for acne", 2 pages.

Photocure ASA e-mail press release dated May 28, 2010, "Photocure ASA (NO)—Photocure announces results from phase II study in acne with Visonac (TM)", 3 pages.

Photocure ASA press release, "Photocure's newly developed Aktilite® CL512 lamp has received CE mark", Published Sep. 9, 2008, 2 pages.

Sagentia Group, "Sagentia undertakes full 'concept through to manufacture' development of acne treatment lamp", Nov. 27, 2008, http://www.sourcewire.com/releases/rel_display.php?relid=43721&hilite.

Sagentia, "Full concept through to manufacture development of acne treatment lamp", Nov. 26, 2008, http://www.sagentia.com/news/press-releases-and-news/2008/photocure.aspx, 4 pages.

Sagentia, "Making light of development challenge: New Electronics", Nov. 27, 2008, http://www.sagentia.com/news/press-coverage/2008/makinglightofdevelopmentchallenge_newelectronics.aspx, 3 pages.

Sagentia, "Photocure—Concept to manufacture development of LED-based treatment lamp", May 19, 2009, http://www.sagentia.com/resources/case-studies/2009/photocure.aspx, 4 pages.

The Gen, News from Sagentia, "Full 'concept through to manufacture' development of acne treatment lamp", Spring 2009, http://www.sagentia.com/resources/articles/2009/gen-spring-09_news_photocure.aspx, 12 pages.

International Search Report from International Patent Application No. PCT/EP2013/067982, mailed on Oct. 10, 2013.

Shaaban et al., "Photodynamic therapy with intralesional 5-aminolevulinic acid and intense pulsed light versis intense pulsed light alone in the treatment of acne vulgaris: a comparative study," Dermatologic Therapy, vol. 25, 2012, 85-91.

* cited by examiner

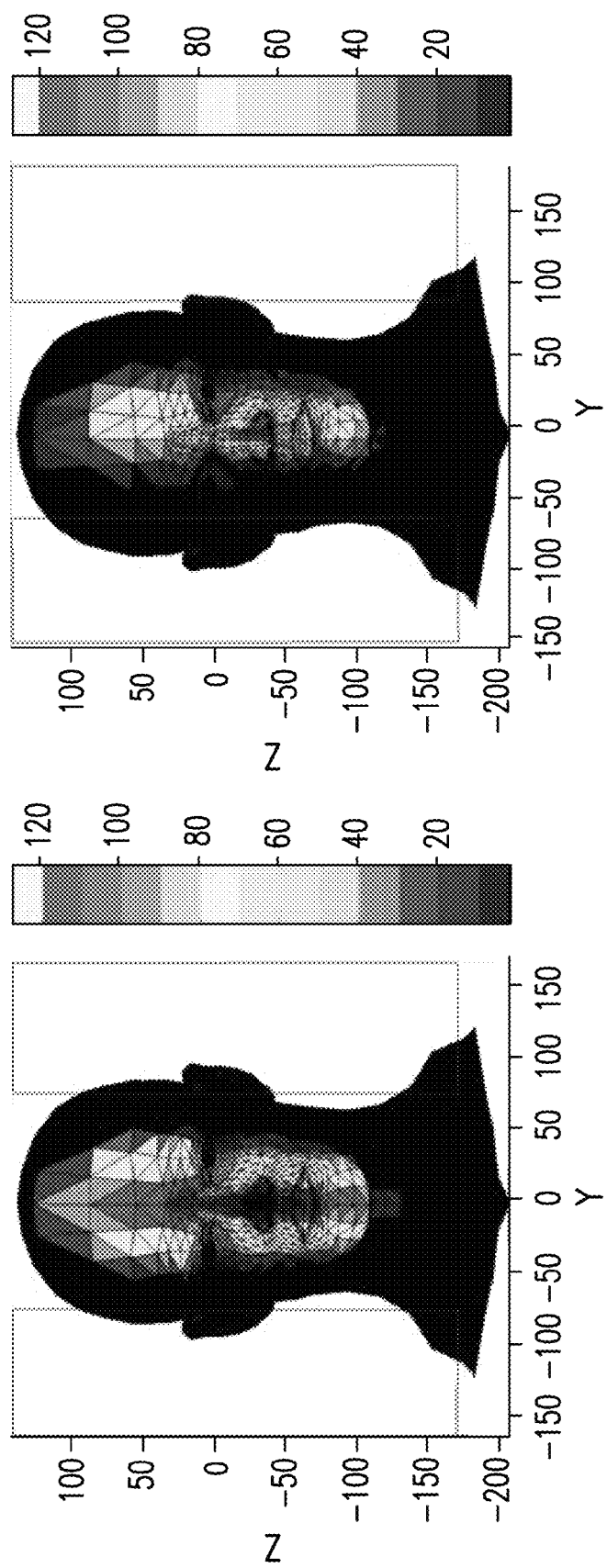

METHODS OF TREATING ACNE USING DUAL PANEL PHOTODYNAMIC THERAPY LAMP

CROSS REFERENCE TO RELATED APPLICATION

The present application claims priority to European Patent Application No. EP 12182486.6, filed in the European Patent Office on Aug. 30, 2012, and is a continuation of U.S. patent application Ser. No. 13/646,274, filed on Oct. 5, 2012, each of which is hereby expressly incorporated herein in its entirety by reference thereto.

FIELD OF THE INVENTION

The present invention relates to a dual panel photodynamic therapy lamp, and a method of using the dual panel photodynamic therapy lamp.

BACKGROUND

Photodynamic therapy (PDT) is a developing therapy used for treatment of various cancers and also for non-malignant diseases including infections, wound-healing and various dermatological diseases. Photodynamic therapy is also used for cosmetic treatment of the skin. PDT involves the administration of a photosensitizer or a precursor thereof to an area of interest. The photosensitizer or precursor thereof is taken up into the cells, where a precursor of a photosensitizer is converted into a photosensitizer. Upon exposure of the area of interest to light, the photosensitizer is excited, usually from a ground singlet state to an excited singlet state. It then undergoes intersystem crossing to a longer-lived excited triplet state. One of the few chemical species present in tissue with a ground triplet state is molecular oxygen. When the photosensitizer and an oxygen molecule are in proximity, an energy transfer can take place that allows the photosensitizer to relax to its ground singlet state, and create an excited singlet state oxygen molecule. Singlet oxygen is a very aggressive chemical species and will very rapidly react with any nearby biomolecules. Ultimately, these destructive reactions will kill cells through apoptosis or necrosis, whereby for instance cancer cells are selectively killed. The mechanisms are still not fully understood, but studies suggest that the clinical result (i.e. the selectivity for cancerous cells) is not due to selective uptake by cancerous cells. Rather, there are similar levels of uptake in all cell types, but the processes of conversion and elimination are different in malignant cells and generally in metabolically active cells, such as inflamed or infected cells, leading to a concentration gradient between cancerous and normal tissue. Clinical experience has shown that PDT has advantages over alternative therapies for treatment of several pathological conditions; including acne, actinic keratosis and various skin cancers. A variation of PDT is PDT which is carried out without a photosensitizer or a precursor thereof, i.e. with light alone (also called phototherapy or light therapy).

U.S. Patent Application Publication No. 2011/0212146, which is incorporated herein in its entirety by reference hereto, describes the use of certain precursors of photosensitizers, i.e., derivatives of 5-aminolevulinic acid (5-ALA), such as for example, 5-ALA esters and salts thereof, in a method of cosmetic treatment of photoaged skin.

U.S. Patent Application Publication No. 2008/0188558, which is incorporated herein in its entirety by reference hereto, describes the use of certain precursors of photosensitizers, i.e., derivatives of 5-aminolevulinic acid (5-ALA), such as for example, 5-ALA esters and pharmaceutically acceptable salts thereof, in a method for photodynamic treatment of acne, e.g. acne vulgaris.

U.S. Patent Application Publication No. 2010/0137439, which is incorporated herein in its entirety by reference hereto, describes PDT, and in particular to the use of 5-aminolevulinic acid (5-ALA) and derivatives of 5-ALA in PDT, in which the side-effects (e.g. pain and/or erythema) of PDT, e.g. of PDT of acne, are prevented or reduced.

Acne is one of the most common human skin diseases, characterized by areas of skin with seborrhea (scaly red skin), comedones (blackheads and whiteheads), papules (pinheads), pustules (pimples), nodules (large papules) and possibly scarring. Acne affects mostly skin with the densest population of sebaceous follicles; these areas include the face, the upper part of the chest, and the back.

One element in safe and efficient PDT, e.g. photodynamic treatment of acne, is the light source, which may include lasers, conventional lamps, or lamps based on light emitting diodes (LEDs).

There are a number of advantages in using LEDs instead of conventional lamps or lasers for PDT. For example, an array of LEDs can be formed to cover a large area. In addition, their high efficiency ensures that less heat dissipation is necessary. Furthermore, LEDs have long term stability and so it is easier to design lamps which are suitable for tens of thousands of hours of operation.

U.S. Patent Application Publication No. 2004/0260365, which is incorporated herein in its entirety by reference hereto, describes a single panel photodynamic therapy lamp comprising a two-dimensional array of LEDs.

U.S. Patent Application Publication No. 2002/0029071 describes an arrangement of 4 panels of LED arrays comprising one panel for directing light to the scalp and 3 panels which are moveably connected to direct light onto the front of the face, the right side of the face and the left side of the face, respectively. Such a 4 panel LED lamp may be used for the treatment of the face and/or scalp, however, the arrangement of 4 panels makes the lamp fairly complex. A 4 panel LED lamp will also have a considerable weight, i.e. requiring suitable support arms and trolleys for moving the lamp. Due to its footprint, it will take up space in hospitals or private practice.

The photodynamic therapy lamps described in U.S. Patent Application Publication No. 2004/0260365 provide a limited treatment area. For example, when used for the photodynamic treatment of acne of a patient's face, as described in U.S. Patent Application Publication No. 2008/0188558, the lamp is not suitable to homogeneously illuminate the face in one illumination session and requires an operator to illuminate each side of the face individually. Likewise, when treating acne of a patient's chest or back, only a part of said chest or back can be treated in one illumination session. As a consequence, the side of the face or the part of the back or chest that is not presently undergoing treatment must be covered by appropriate means to prevent stray, unwanted illumination from impinging on such side or part. Therefore, the photodynamic therapy lamp requires a relatively long treatment time, additional operator functions, and additional materials in order to treat both sides of a patient's face or the entire chest or back. Moreover, the lamp must be precisely positioned independently for each side of the patient's face or each part of the patient's back or chest in order to ensure homogeneous illumination, thereby placing additional burdens on the operator to correctly perform the photodynamic treatment. Thus, in order to ensure correct treatment, the received light dose per side or part of the patient may need to be measured and evaluated, and subsequently, re-treatment of particular areas that did not receive the required light dose may be necessary, thereby further complicating and extending the treatment.

In order to treat a face of a patient suffering from acne, it is not sufficient to simply enlarge the lamps described in U.S. Patent Application Publication No. 2004/0260365 since although an enlarged lamp is able to illuminate the whole face in one illumination session, such an illumination is not homogeneous and thus it is not ensured that the correct light dose is administered to each part of the face.

SUMMARY

According to an exemplary embodiment of the present invention, a photodynamic therapy lamp comprises two lamp modules each lamp module comprising a two-dimensional array of LEDs and each of the lamp modules are configured to be movable between a first position in which an angle between the lamp modules is from 157 degrees to 180 degrees, and a second position in which the angle between the lamp modules is from 50 degrees to 70 degrees.

According to an exemplary variant of the present invention, the angle in the first position is preferably from 163 to 172 degrees, more preferably the angle in the first position is from 166.5 to 170.5 degrees, and most preferably the angle in the first position is 168.5 degrees. A gap between the lamp modules in the first position exists. Said gap in said first position is preferably approximately 16 mm.

According to an exemplary variant of the present invention, the angle in the second position is preferably from 55 to 65 degrees, more preferably the angle in the second position is from 58 to 62 degrees, and most preferably the angle in the second position is 60 degrees. A gap between the lamp modules in the second position exists. Said gap in said second position is preferably approximately 136 mm.

According to an exemplary variant of the present invention, the LEDs are collimated LEDs. The term "collimated" in the context of the invention means that the rays of light from each LED have reduced divergence without being perfectly parallel such that there is some overlap of rays from one LED with neighboring LEDs. The collimated LEDs include optical mirrors or lenses, preferably lenses. In a preferred embodiment a single lens is provided for each LED.

According to an exemplary variant of the present invention, the lamp modules are identical.

According to an exemplary variant of the present invention, the lamp modules are substantially flat.

According to an exemplary variant of the present invention, the lamp modules include locking elements configured to lock the lamp modules in the first and second positions.

According to an exemplary variant of the present invention, the lamp modules include visual markings configured to indicate the first and second positions.

According to an exemplary variant of the present invention, each lamp module comprises a housing, within the housing there is provided the two-dimensional array of LEDs.

According to an exemplary variant of the present invention, each lamp module comprises a housing having an optical window which, when the photodynamic therapy lamp is in use, faces the treatment surface of a patient.

According to an exemplary variant of the present invention, when the photodynamic therapy lamp is in use, a distance between the lamp modules and a treatment surface of a patient is between about 5 cm to about 8 cm.

According to an exemplary variant of the present invention, the optical window and thus the surface of each lamp module comprising said optical window is substantially flat.

According to an exemplary variant of the present invention, each lamp module further comprises a substrate on which the array of LEDs is mounted and a heat sink. In a preferred embodiment, the substrate is the heat sink.

According to an exemplary variant of the present invention, each lamp module comprises a housing having an optical window, within the housing there is provided the two-dimensional array of LEDs, a substrate on which the array of LEDs is mounted, a heat sink, a cooling unit configured to cool the array of LEDs and at least one driver module. In a preferred embodiment, the substrate is the heat sink.

According to an exemplary variant of the present invention, the cooling unit includes at least one fan, preferably a fan configured to provide forced-air cooling of the array of LEDs.

According to an exemplary variant of the present invention each array of LEDs includes an identical number of LEDs. Each LED array preferably contains 144 LEDs or more, more preferably 192 LEDs or more, even more preferably from 240 to 320 LEDs and most preferably 256 LEDs.

According to an exemplary variant of the present invention each array of LEDs is rectangular.

According to an exemplary variant of the present invention the array of LEDs is formed of individual LED array elements that are arranged in a regular pattern, preferably in a honeycomb pattern (i.e. hexagonal array) as described in U.S. Patent Application Publication No. 2004/0260365.

According to an exemplary variant of the present invention each LED emits red light, preferably red light at a nominal wavelength of approximately 632 nm±5 nm, and more preferably a nominal wavelength of 636 nm. According to another exemplary variant of the present invention each LED emits blue light, preferably blue light at a nominal wavelength of approximately 417±5 nm. According to another exemplary variant of the present invention each array of LEDs consists of a subset of LEDs that emits red light and another subset of LEDs that emits blue light. Preferably, each subset contains the same number of LEDs.

According to an exemplary variant of the present invention an irradiance (fluence rate) of the array of LEDs is from 30 to 150 mW/cm$^2$, preferably from 40 to 100 mW/cm$^2$ and most preferably from 46 mW/cm$^2$ to 68 mW/cm$^2$, e.g. 46 mW/cm$^2$ and 68 mW/cm$^2$.

According to an exemplary variant of the present invention a light dose of the array of LEDs is from about 1 to 99 J/cm$^2$, more preferably from 5 to 80 J/cm$^2$ and most preferably from 10 to 70 J/cm$^2$.

According to an exemplary variant of the present invention, the lamp further comprises a base, preferably a moveable base and a support arm movably connecting the two lamp modules with the base.

According to an exemplary variant of the present invention, the base includes a power source, control electronics, and a patient cooling unit. The patient cooling unit includes a fan and an outlet operable by the patient.

According to an exemplary variant of the present invention, the lamp further comprises a user interface having at least one input device and at least one output device.

According to an exemplary embodiment of the present invention, a method of using a photodynamic therapy lamp comprising two lamp modules each lamp module comprising a two-dimensional array of LEDs and each of the lamp modules are configured to be movable between a first position in which an angle between the lamp modules is from 157 degrees to 180 degrees, and a second position in which the angle between the lamp modules is from 50 degrees to 70 degrees.

According to an exemplary variant of the present invention, the method further comprises positioning the lamp modules in the first or second position, preferably locking the lamp modules in said first or second position by means of locking elements.

According to an exemplary variant of the present invention, the method further comprises prior to positioning the lamp modules in the first or second position, administering a composition comprising a photosensitizer or a precursor of a photosensitizer to a treatment area on a patient and optionally waiting for a period (incubation time).

According to an exemplary variant of the present invention, the method further comprises aligning the lamp modules to a treatment area on a patient for optimal treatment, preferably by illuminating the treatment area with a subset of the LEDs from the array of LED to determine the correct positioning of the lamp modules in relation to the treatment area. The aligning of the lamp modules in the first position includes positioning the lamp modules a predetermined distance from the treatment area. The predetermined distance is preferably from about 5 cm to about 8 cm.

According to an exemplary variant of the present invention, the method further comprises inputting parameters of a photodynamic treatment via a user interface, and performing the treatment based on the inputted parameters.

According to an exemplary variant of the present invention, the performing the treatment includes emitting light from the array of LEDs of one or both lamp modules.

According to an exemplary variant of the present invention, the method further comprises cooling the patient by a patient cooling unit including a fan and an outlet operable by the patient.

According to an exemplary embodiment of the present invention, a method of using a photodynamic therapy lamp comprising two lamp modules each lamp module comprising a two-dimensional array of LEDs and each of the lamp modules are configured to be movable between a first position in which an angle between the lamp modules is from 157 degrees to 180 degrees, and a second position in which the angle between the lamp modules is from 50 degrees to 70 degrees, in which the lamp is configured to be used with a composition comprising a photosensitizer or a precursor of a photosensitizer, preferably with a composition comprising a precursor of a photosensitizer. In a preferred embodiment, the precursor of a photosensitizer is 5-ALA or a pharmaceutically acceptable salt thereof or a derivative of 5-ALA or a pharmaceutically acceptable salt thereof. In a more preferred embodiment, the precursor of a photosensitizer is a derivative of 5-ALA or a pharmaceutically acceptable salt thereof, more preferably a 5-ALA ester or a pharmaceutically acceptable salt thereof.

According to an exemplary embodiment of the present invention, a method of using a photodynamic therapy lamp comprising two lamp modules each lamp module comprising a two-dimensional array of LEDs and each of the lamp modules are configured to be movable between a first position in which an angle between the lamp modules is from 157 degrees to 180 degrees, and a second position in which the angle between the lamp modules is from 50 degrees to 70 degrees, said method comprising (i) applying a composition comprising a photosensitizer or a precursor of a photosensitizer to a treatment area on a patient, (ii) optionally waiting for a period (incubation time), (iii) positioning the lamp modules in one of the first and second positions such that the array of LEDs face the treatment area and (iv) performing the photodynamic treatment.

According to an exemplary embodiment of the present invention, a method of using a photodynamic therapy lamp comprising two lamp modules each lamp module comprising a two-dimensional array of LEDs and each of the lamp modules are configured to be movable between a first position in which an angle between the lamp modules is from 157 degrees to 180 degrees, and a second position in which the angle between the lamp modules is from 50 degrees to 70 degrees, said method comprising (i) positioning the lamp modules in one of the first and second positions such that the array of LEDs face the treatment area and (ii) performing the photodynamic treatment.

BRIEF DESCRIPTION OF THE DRAWINGS

FIGS. 9B, 9C and 9D show the results of a 3D illumination modeling of a human's face illuminated by a two rows from each array of LEDs of a photodynamic therapy lamp according to the invention with the lamp modules in the second position, wherein the lamp is not optimally positioned in relation to the human's face.

DETAILED DESCRIPTION

Figure 1:
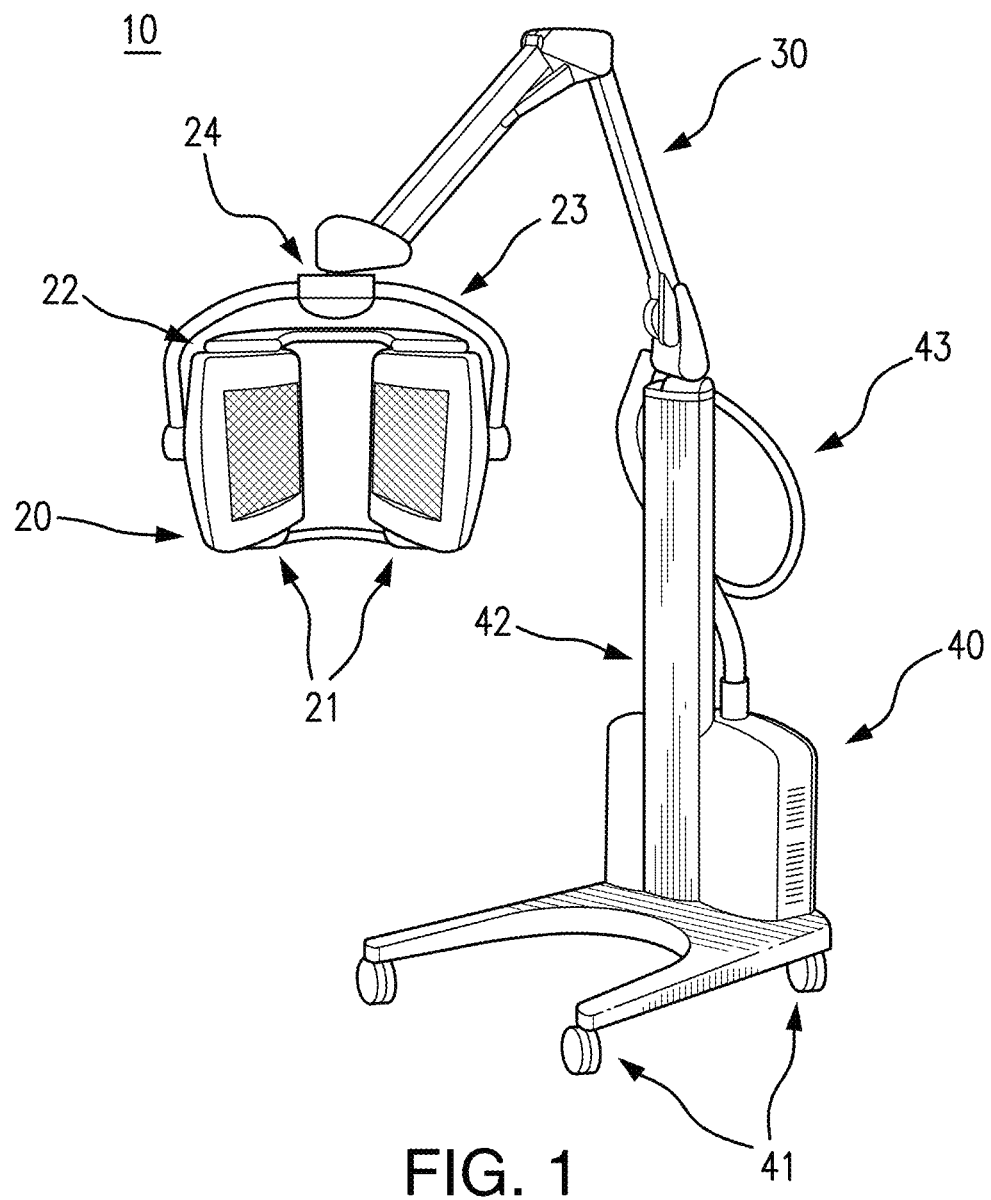
FIG. 1 illustrates an exemplary embodiment of a photodynamic therapy lamp according to the present invention.

According to the present invention, a photodynamic therapy lamp having two lamp modules (hereinafter lamp modules or modules) in a housing is provided, in which the modules are connected via a hinge. In a planar orientation, i.e. a first position, the two LED lamp modules may be oriented substantially parallel with each other in substantially the same plane such that the modules evenly illuminate a relatively flat surface. That is, in the planar orientation, i.e. the first position, the angle between the two lamp modules is from 157 degrees to 180 degrees, more preferably from 163 degrees to 172 degrees, even more preferably from 166.5 degrees to 170.5 degrees, and most preferably 168.5 degrees. In an exemplary embodiment of the present invention, a gap may be present between the two modules in the first position due to the modules being provided in a housing. Thus, in order to homogeneously illuminate a treatment area in a substantially planar orientation, the two lamp modules may be slightly angled toward each other. In an alternative exemplary embodiment in which there is no gap between the two lamp modules in a planar orientation, no angling of the two lamp modules toward each other may be necessary to homogeneously illuminate a treatment area. Hence, in such alternative exemplary embodiment the angle between the two lamp modules in a first position may be 180 degrees.

In an alternative angled orientation, i.e. a second position, each of the lamp modules may be rotated towards the other lamp module such that each module illuminates in a direction at least partially facing the other lamp module. That is, in the angled orientation, i.e. the second position, the angle between the two lamp modules is from 50 degrees to 70 degrees, preferably from 55 degrees to 65 degrees, more preferably from 58 degrees to 62 degrees, and most preferably 60 degrees.

In the planar orientation, i.e. first position, of the lamp modules, the lamp according to the present invention may be used to treat relatively flat surfaces of a patient, e.g., a patient's chest or back. In the angled orientation, i.e. second position, of the lamp modules the lamp according to the present invention may be used to treat contoured surfaces of a human, e.g., a patient's face.

Due to the provision of two lamp modules and positioning the lamp modules in the described planar and angled orientation, the photodynamic therapy lamp according to the invention can be used for the treatment of larger, relatively flat surfaces of a patient at a single time as well as for the treatment of contoured surfaces of a patient. Moreover, due to positioning the two lamp modules in the specific angles described for the first and second position, the selected treatment area (e.g. larger relatively flat surfaces and contoured surface of a patient) are homogeneously illuminated. Thus all parts of the selected treatment area receive the same light dose, thereby facilitating shorter treatment times, fewer required operator functions for treatment, and most importantly, ensuring a safe and efficient treatment. In this regard, photodynamic treatment success is dependent on both drug dose and light dose. For example, if a part of a treatment area receives a light dose which is greater than what is required, potential treatment side effects including pain, redness and/or edema can occur. On the other hand, if a part of the treatment area receives a light dose which is less than what is required, potential treatment failures include ineffective/insufficient treatment, and/or potential re-treatment Thus it is clear that the photodynamic therapy lamp according to the invention provides an advantage over the lamps of the prior art, e.g. over the lamps described in U.S. Patent Application Publication No. 2004/0260365 which only provide a limited treatment area. For example, when used for the photodynamic treatment of a larger, relatively flat surface of a patient or a contoured surface of a patient such as the face, only a part of this treatment area can be treated in one illumination session. As a consequence, the part of the treatment area that is not presently undergoing treatment must be covered by appropriate means to prevent stray, unwanted illumination from impinging on such part. Therefore, the use of the lamps described in U.S. Patent Application Publication No. 2004/0260365 in photodynamic therapy requires a relatively long treatment time, additional operator functions, and additional materials in order to the entire treatment area. Moreover, the lamp must be precisely positioned independently for each part of the treatment area in order to ensure homogeneous illumination, thereby placing additional burdens on the operator to correctly perform the photodynamic treatment. Thus, in order to ensure correct treatment, the received light dose per part of treatment area may need to be determined (e.g. measured and evaluated), and subsequently, re-treatment of particular parts that did not receive the required light dose may be necessary, thereby further complicating and extending the treatment.

In order to maintain the precise positioning of the lamp modules according to the present invention in either of the planar or angled orientations, i.e. first and second position, the photodynamic therapy lamp according to the invention may be provided with locking positions and/or locking elements that facilitate correct positioning of the lamp modules in the first and second position and that prevent unwanted movement of the lamp modules during treatment. For example, a locking element may hold each lamp module in the first position, and the same or a different locking element may hold each lamp module in the second position. In addition, the locking positions and/or locking elements may provide positive feedback to an operator in order to ensure precise positioning of the lamp modules for treatment, thereby further reducing potential sources of error.

The two lamp modules of the photodynamic therapy lamp according to the invention each comprise a two-dimensional array of LEDs, preferably a rectangular array of LEDs. Each array of LEDs preferably includes an identical number of LEDs. In general the number of LEDs should be sufficient to ensure complete illumination of the treatment area, e.g. the face. However, minimizing the number of LEDs is important since the cooling requirements and the overall weight and size of the lamp modules can be reduced which also impacts of overall costs and complexity. Each array of LEDs comprised in the two lamp modules of the photodynamic therapy lamp according to the invention preferably contains 144 LEDs or more, more preferably 192 LEDs or more, even more preferably from 240 to 320 LEDs and most preferably 256 LEDs. In one embodiment, the array of LEDs is formed of individual LED array elements that are arranged in a regular pattern, preferably in a honeycomb pattern (i.e. hexagonal array) as described in U.S. Patent Application Publication No. 2004/0260365. For an array of LEDs which consists of 256 LEDs, said LEDs are preferably arranged in a regular pattern made of 16 individual LED array elements, each of said elements consisting of 16 LEDs.

The LEDs are preferably collimated LEDs and the lamp modules of the photodynamic therapy lamp of the invention comprise optical mirrors or lenses, preferably lenses, configured to collimate light emitted from the LEDs. In a preferred embodiment, the lenses are provided in the form of an array of lenses, preferably an array of lenses that matches the array of LEDs such that a single lens is provided for each LED. Thus, the two lamp modules of the photodynamic therapy lamp according to the invention preferably each comprise a two-dimensional array of LEDs and a two-dimensional array of lenses, preferably a rectangular array of LEDs and a rectangular array of lenses, and the number of LEDs in said array of LEDs corresponds to the number of lenses in said array of lenses. As an example, in a most preferred embodiment, each lamp module of the photodynamic therapy lamp according to the invention comprises a two-dimensional array of LEDs which consists of 256 LEDs and a matching two-dimensional array of lenses which consists of 256 lenses. In a further preferred embodiment, said 256 LEDs are arranged in a regular pattern made of 16 individual LED array elements, each of said elements consisting of 16 LEDs and said 256 lenses are arranged in a regular pattern made of 16 individual lens array elements, each of said elements consisting of 16 lenses.

FIG. 1 illustrates an exemplary embodiment of a photodynamic therapy lamp 10 according to the present invention. The lamp 10 includes a lamp head 20, a support arm 30, and a base 40.

The lamp head 20 comprises two adjacent, substantially flat lamp modules 21 comprising each a two-dimensional array of LEDs and a housing, a hinge 22, a yoke 23 and a user interface. The two lamp modules 21 are connected to each other by a hinge 22 which allows the lamp modules 21 to be individually moved relative to each other, i.e. rotated towards and from each other to be positioned for treatment. In order to maintain the precise positioning of the lamp modules according to the present invention in either of the planar or angled orientations, i.e. first and second position, the hinge 22 preferably comprises elements to lock the lamp modules in said first and second position (locking elements) and that prevent unwanted movement of the lamp modules during treatment. For example, a locking element may hold each lamp module in the first position, and the same or a different locking element may hold each lamp module in the second position. In addition, the locking elements may provide positive feedback to an operator in order to ensure precise positioning of the lamp modules for treatment, thereby further reducing potential sources of error.

The lamp head 20 further comprises a yoke 23 which connects the two lamp modules 21 to the support arm 30. A rotating joint is preferably present at the connection of the yoke 23 and each lamp module 21 which permits the two lamp modules 21 to be rotated about a horizontal "x" axis, thus being able to be positioned into a position wherein the array of LEDs face towards a vertically oriented treatment area, e.g. the face, chest or back of a sitting patient or towards a horizontally oriented treatment area, e.g. the face, chest or back of a lying patient. Further, a rotating joint is preferably present at the connection of the yoke 23 and the support arm 30 which permits the lamp head 20 to be rotated about a vertical "z" axis. This provides the operator with an easy access to a user interface 24. A user interface 24 may be provided for controlling the lamp 10. For example, the user interface may include an input device, such as a keyboard or keypad, and an output device, such as a display, an LCD display and/or an audio output. The user interface may be situated on the lamp head 20 and configured to drive the LEDs. The user interface may control power sequencing, and monitor and report faults in the lamp 10.

The support arm 30 is connected at one end to the base 40, and is connected at the other end to the lamp head 20. The support arm allows the lamp head 20 to be moved relative to the base 40. The support arm 30 may be a self-balancing arm that is configured to suspend the lamp head 20 in the desired position for treatment, e.g. in a position for the treatment of a patient's face, back or chest and to maintain this position without drift for the duration of the treatment.

The base 40 may include a power source, and/or may include a connection to an external power source. In addition, the base 40 may include wheels 41, and associated brakes, so that the photodynamic therapy lamp 10 can be moved and temporarily held stationary. The base 40 may include a trolley, e.g., a mobile stand with wheels and associated brakes, that allows the lamp 10 to be moved to a site of treatment and maneuvered for access. An integrated vertical pillar 42 of the base 40 may provide an anchor point for the support arm 30 and ensures that the lamp head 20 is held at a height suitable for treatment of a sitting or lying patient, e.g. a patient sitting on a chair or lying on a bed. Further, the base 40 may also house the power supply and electronics for the lamp 10, and an optional patient cooling unit 43 having a fan that draws in ambient air and a cooling air outlet, e.g., hose/duct, controllable by the patient/operator. Alternatively, the base 40 may be configured as a table mounted support and/or a wall mounted support.

Figure 2A:
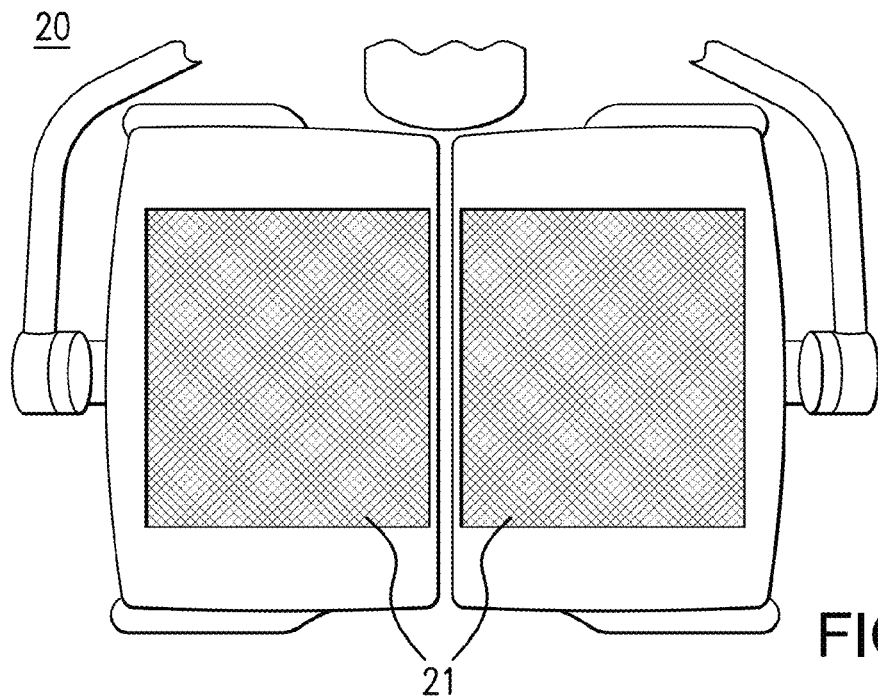
FIG. 2A illustrates the lamp modules of the photodynamic therapy lamp illustrated in FIG. 1 in the first position.
Figure 2B:
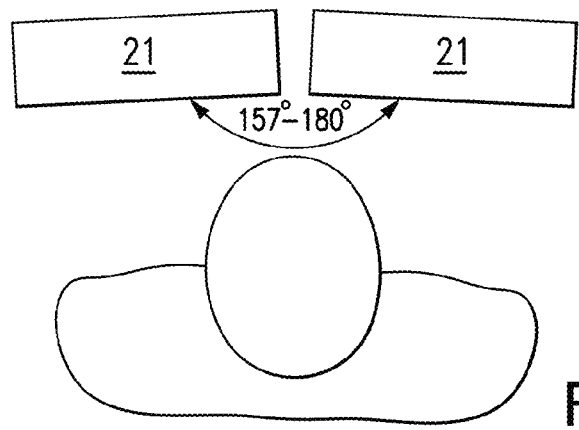
FIG. 2B schematically illustrates the lamp modules of FIG. 2A being positioned over a lying patient's chest or in front of a sitting patient's chest for photodynamic treatment of said patient's chest.
Figure 2C:
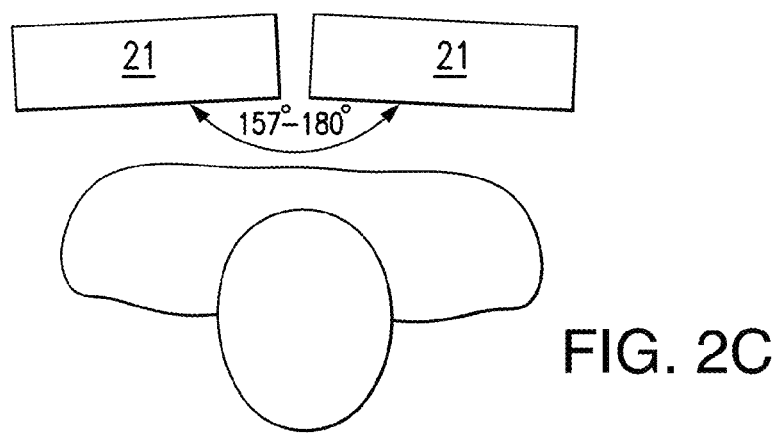
FIG. 2C schematically illustrates the lamp modules of FIG. 2A being positioned over a lying patient's back or behind a sitting patient's back for photodynamic treatment of said patient's back.

FIGS. 2A, 2B and 2C illustrate a planar orientation of the lamp modules 21 of the exemplary embodiment of a photodynamic therapy lamp 10 according to the present invention. In the planar orientation, i.e. first position, the lamp modules 21 are situated substantially parallel with each other and facing the same direction, such that an angle between the two lamp modules 21 is from 157 degrees to 180 degrees, more preferably from 163 degrees to 172 degrees, even more preferably from 166.5 degrees to 170.5 degrees, and most preferably 168.5 degrees. In addition, in the planar orientation, the inner edges of the two lamp modules 21 may be separated from each other by a gap of approximately 16 mm 2 mm. In this planar orientation, a larger surface area may be treated at a single time, thereby facilitating shorter treatment times and fewer required operator functions for treatment. Such a larger surface area may be the chest of a patient, as illustrated in FIG. 2B which shows the treatment of a lying patient's chest (viewed from the anterior end) or sitting patient's chest (top view). Further, such a larger surface area may be the back of a patient, as illustrated in FIG. 2C, which shows the treatment of a lying patient's back (viewed from the anterior end) or sitting patient's back (top view).

Figure 3A:
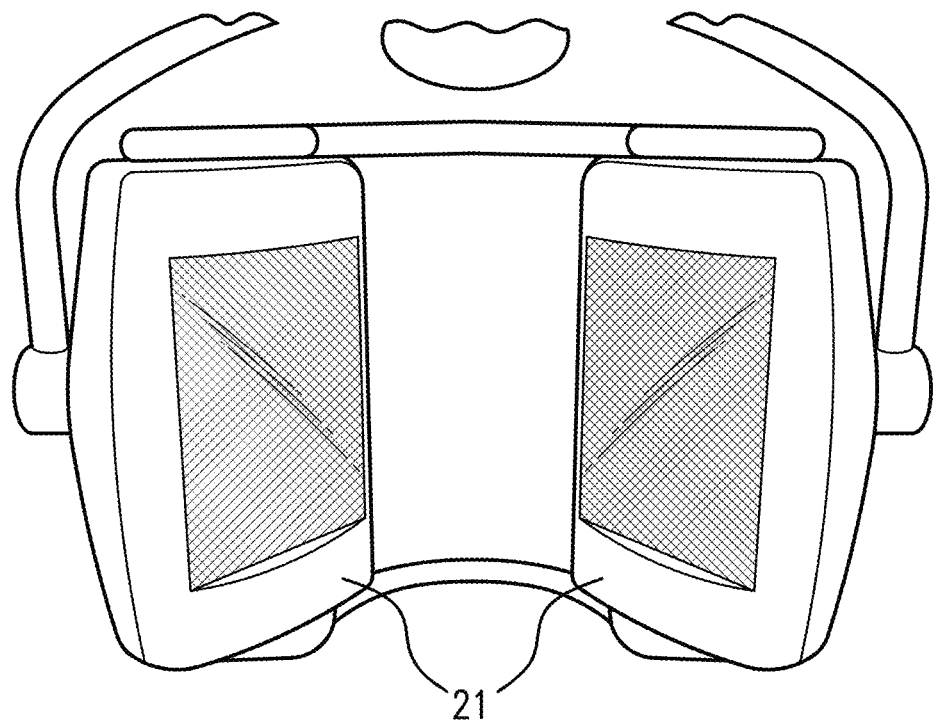
FIG. 3A illustrates the lamp modules of the photodynamic therapy lamp illustrated in FIG. 1 in the second position.
Figure 3B:
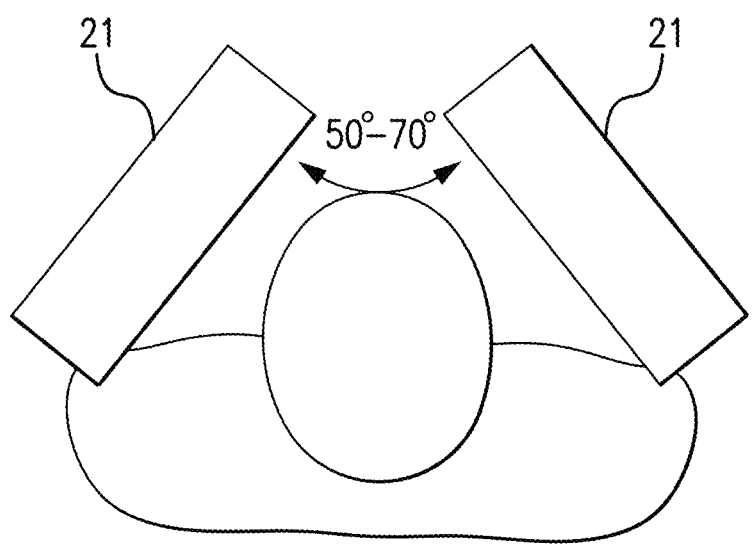
FIG. 3B schematically illustrates the lamp modules of FIG. 3A being positioned over a lying patient's face or in front of a sitting patient's face for photodynamic treatment of said patient's face.

FIGS. 3A and 3B illustrate an angled orientation of the lamp modules 21 of the exemplary embodiment of a photodynamic therapy lamp 10 according to the present invention. In the angled orientation, i.e. the second position, the lamp modules 21 are rotated relative to each other and at least partially facing toward each other, such that an angle between the two lamp modules 21 is from 50 degrees to 70 degrees, preferably from 55 degrees to 65 degrees, more preferably from 58 degrees to 62 degrees, and most preferably 60 degrees. In addition, in the angled orientation, the inner edges of the two lamp modules 21 may be separated from each other by a gap of approximately 136 mm±2 mm. In this angled orientation, a contoured surface may be treated, e.g. a patient's face as illustrated in FIG. 3B which shows the treatment of a sitting patient's face (top view) or lying patient's face (viewed from the anterior end).

FIG. 4 illustrates one of the two lamp module 21 of the exemplary embodiment of a photodynamic therapy lamp 10 according to the present invention. FIG. 4A shows a front view of a lamp module 21 with a housing 25 comprising a front enclosure 25a and a rear enclosure 25b (not visible) and a two-dimensional array of LEDs (not visible) which is covered by a matching two-dimensional array of lenses 26. Preferably, the array of lenses is covered by an optically clear window, e.g. a polymer window through which light from the LEDs is emitted for treatment. Preferably, one lamp module 21 includes 256 LEDs 27 which are mounted on a substantially flat support. The type of LED is dependent on the wavelength selected for treatment which in turn is dependent on the photosensitizer which is used in the photodynamic treatment. In general, the type of LED is selected to have an emission spectrum substantially coincident with the absorption spectrum of the photosensitizer. The absorption spectrum of most photosensitizers shows several peaks, i.e. more than one wavelength may be suitable to excite the photosensitizer. In this case the wavelength may also be selected according to the penetration depth. In general red light penetrates deeper into the skin than for instance blue light, thus being able to reach and treat deeper layers and structures in the skin, e.g. the sebaceous glands in the case of an acne treatment. LEDs are commercially available from various suppliers. Preferred LEDs for the photodynamic therapy lamp of the invention are the Luxeon Rebel emitters produced by Lumileds®. The individual LEDs are preferably arranged in a regular pattern of 16×16 LEDs, preferably in a honeycomb pattern as shown in FIG. 4B. The array of LEDs is covered by a matching array of lenses 26, e.g., made of polycarbonate, that are configured to collimate the light emitted from the LEDs. For example, the individual LEDs array elements may be arranged in a honeycomb pattern with a 12.9 mm pitch or center-to-center distance.

The LEDs may emit red light, preferably red light having a nominal wavelength of approximately 632 nm±5 nm, preferably 636 nm. Alternatively, the LEDs may emit blue light, preferably blue light at a nominal wavelength of approximately 417 nm±5 nm. In another embodiment, each array of LEDs consists of a subset of LEDs which emits red light and of another subset of LEDs which emits blue light. In a preferred embodiment, the number of LEDs in each subset is identical. In another preferred embodiments, each array of LEDs consists of alternating blue light emitting LEDs and red light emitting LEDs.

The efficacy of the LEDs for PDT is temperature dependent. That is, with higher temperatures when the lamp 10 is in use and the LEDs generate heat, there is a reduction in luminous output and a shift of wavelength to a higher wavelength. A reduced luminous output requires an extension of the illumination time to achieve a predetermined light dose. Thus, if the temperature of the LEDs is not controlled, the illumination time may be variable and extended to achieve the predetermined light dose. By controlling the temperature of the LEDs using an appropriate cooling system, the illumination time may be set as a fixed parameter. In a preferred embodiment, in order to ensure delivery of the predetermined light dose, the drive current for the LEDs is variable and adapted in operation to meet delivery of the light dose within a fixed illumination time. The output of the lamp modules 21 may be preferably varied between a high irradiance (fluence rate) and a low irradiance (fluence rate), e.g. a high fluence rate of approximately 150 mW/cm$^2$ and a low fluence rate of approximately 30 mW/cm$^2$. In a preferred embodiment, the output of the lamp modules 21 may be preferably varied between a high fluence rate of approximately 68 mW/cm$^2$ and a low fluence rate of approximately 46 mW/cm$^2$. Further, the light dose may be varied between 1 and 99 J/cm$^2$. For example, the light dose may be approximately 10 J/cm$^2$ when blue light is used for the treatment of acne or actinic keratosis or 37 J/cm$^2$ when red light is used for the treatment of actinic keratosis or acne or for a cosmetic treatment of photoaged skin.

The lamp modules 21 may preferably include a cooling system to maintain the temperature of the LEDs for optimal performance. Preferably, the lamp modules 21 may be cooled by forced-air cooling. For example, each lamp module 21 may include heat sinks to which the LED arrays are directly mounted, and fans and associated ducts behind each array of LEDs that provide effective forced-air cooling. Alternatively or additionally, the lamp module 21 may be cooled by convective air cooling using, for example, heat sinks, and/or by liquid cooling using a coil and pump. The choice of cooling system may depend on various factors, including, for example, weight, cost, complexity, temperature uniformity, noise, and reliability.

Figure 4B:
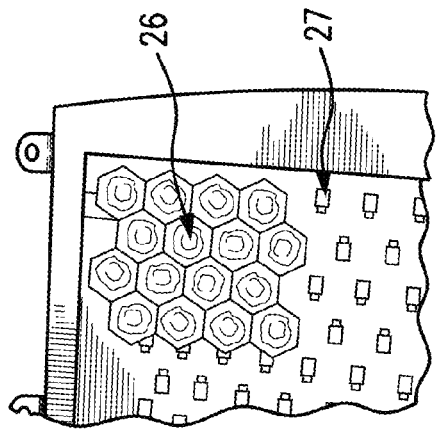
FIG. 4B illustrates the array of LEDs and array of lenses in a part of the lamp module of FIG. 4A.
Figure 4A:
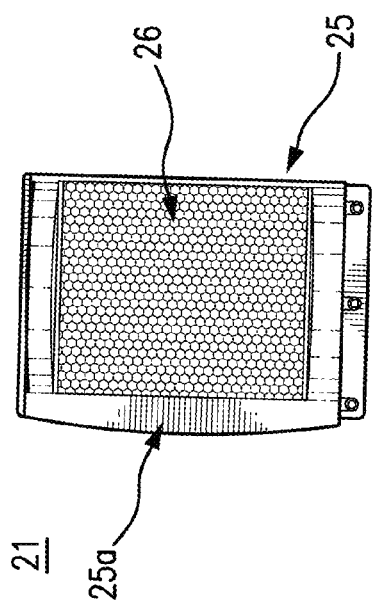
FIG. 4A illustrates the front of a single lamp module of the photodynamic therapy lamp illustrated in FIG. 1
Figure 4D:
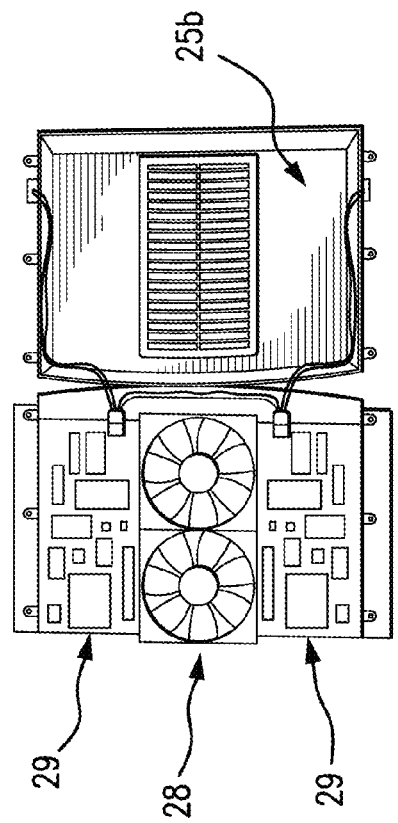
FIG. 4D illustrates the rear enclosure and further components of the lamp module of FIG. 4A.
Figure 4C:
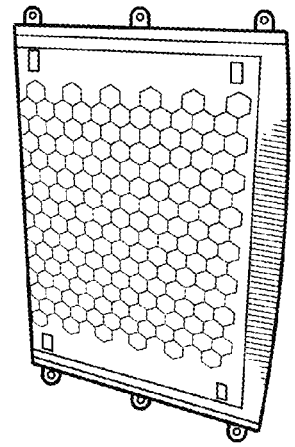
FIG. 4C illustrates the array of lenses in the lamp module of FIG. 4A.

The LEDs may be mounted on a support made of aluminum, for example, with low thermal resistance, and the support may in turn be thermally bonded to a heat-sink also made of aluminum, for example. In a preferred embodiment, the support is the heat-sink, i.e. the LEDs are mounted to the heat-sink as illustrated in FIG. 4C. Further, the support and/or heat sink of each lamp module 21 may be mounted to one or more cooling fans 28 and associated ducts for cooling, and one or more driver modules 29 for control of the lamp module 21 as illustrated in FIG. 4D. Each lamp module 21 may include two driver boards such that each driver board drives half of the LEDs of each module, e.g., 128 LEDs.

Each lamp module 21 comprises a housing 25 which comprises a front enclosure 25a and a rear enclosure 25b, e.g. plastic injection molded front and rear enclosures made of ABS (acrylonitrile butadiene styrene). Each lamp module 21 may be assembled using various joining methods, including, for example, ultrasonic welding, adhesives, and/or fasteners.

Preferably, the photodynamic therapy lamp 10 comprises locking elements to position and maintain the lamp modules 21 in the angled and/or planar orientations, i.e. in the first and second position. For example, the locking elements may include positive detents provided at the first and second position of each of the lamp modules 21. Additionally or alternatively, the lamp modules 21 and/or lamp head 20 may include markings to visually aid an operator in positioning and/or verifying the lamp modules 21 in the first and second position. For example, a locking element may hold each lamp module in the first position, and the same or a different locking element may hold each lamp module in the second position. In addition, the locking elements may provide positive feedback to an operator in order to ensure precise positioning of the lamp modules for treatment, thereby further reducing potential sources of error.

Figure 5:
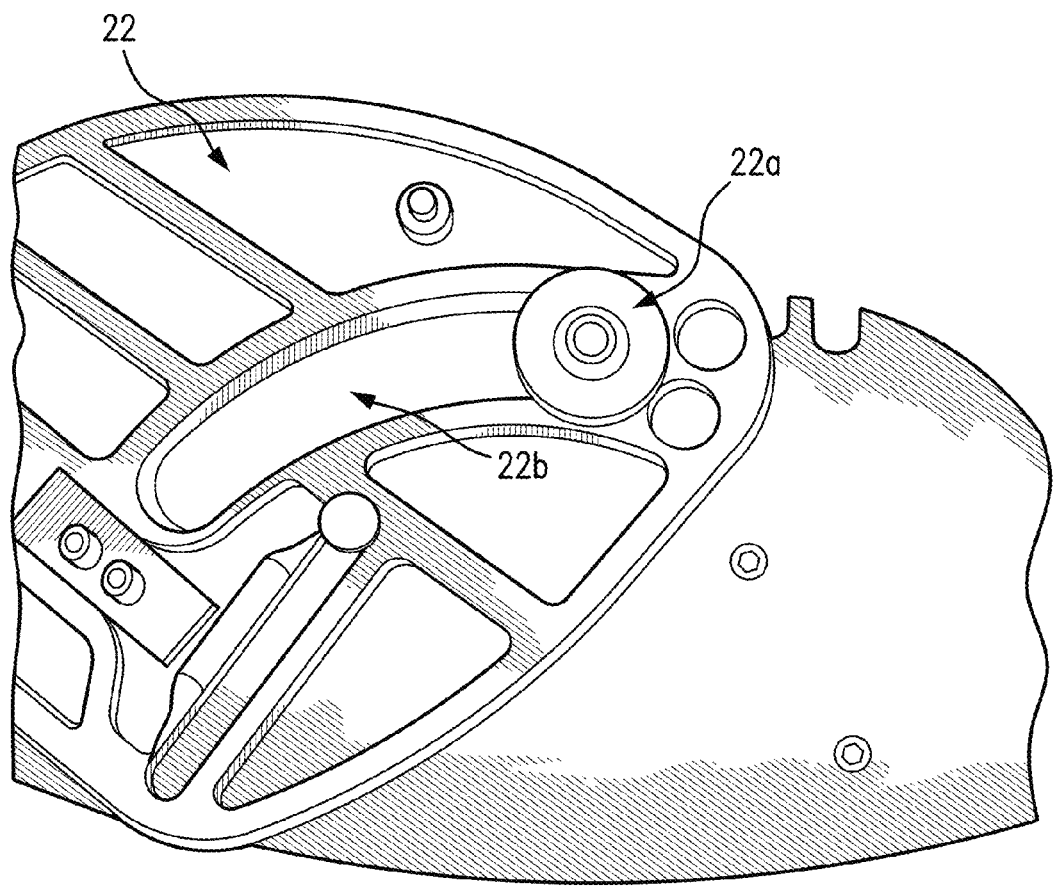
FIG. 5 illustrates locking elements of the lamp modules of the photodynamic therapy lamp illustrated in FIG. 1.

FIG. 5 illustrates the locking elements of one of the lamp modules 21 of a photodynamic therapy lamp 10 according to the present invention. The second lamp module 21 is not shown but preferably comprises identical locking elements. The locking elements are part of the hinge 22 and comprise a bearing disc 22a and a guide slot 22b. The bearing disc 22a rests at the end of the guide slot 22b in the first and second position, respectively. When the lamp module is moved from the first into the second position (or vice versa), the bearing disc slides in the guide slot until it comes to rest at said second position. In a preferred embodiment, the center of mass of the lamp head 20 shall not move by more than ±10 mm from the nominal position when the two lamp modules 21 are moved from the first to the second position (and vice versa) in such a way that they remain symmetrically positioned about the lamp head 20 centerline at all times during the motion.

As mentioned earlier, it is important for the efficacy and safety of a photodynamic treatment that the treated area is homogeneously illuminated and that the same light dose is provided to all parts of said treatment area. As an example, in order to treat the face of a patient suffering from acne, it is not sufficient to simply enlarge the photodynamic therapy lamps described in U.S. Patent Application Publication No. 2004/0260365 since although an enlarged lamp is able to illuminate the whole face in one illumination session, such an illumination is not sufficiently homogeneous and thus it is not ensured that the correct light dose is provided to each part of the face.

FIG. 6 show the results of 3D mathematical model of the illuminance of a patient's face/head with a lamp according to U.S. Patent Application Publication No. 2004/0260365. The model is based on the geometry and size of a fairly large human head which is covered by a triangular mesh and on the illumination of said head with light emitted from a lamp module comprising an array of LEDs which is described as a regular grid of LEDs over a polygon. Thus, any array of LEDs can be modeled. The assumption is made that the LEDs are at some distance from the surface of the lamp module, i.e. accounting for lenses configured to collimate light emitted from said LEDs, e.g. for an array of lenses and for an optical window. The LEDs are modeled as a point source with some angular intensity function. It is further assumed that the illuminance is uniform over each triangle of the triangular mesh. Based on said model, the illuminance from each LED is calculated at each triangle. The results of the calculation are displayed in color ranging from a red color for the strongest illumination (highest intensity) to a dark blue color for the weakest illumination (lowest intensity).

Figures 6A, 6B:
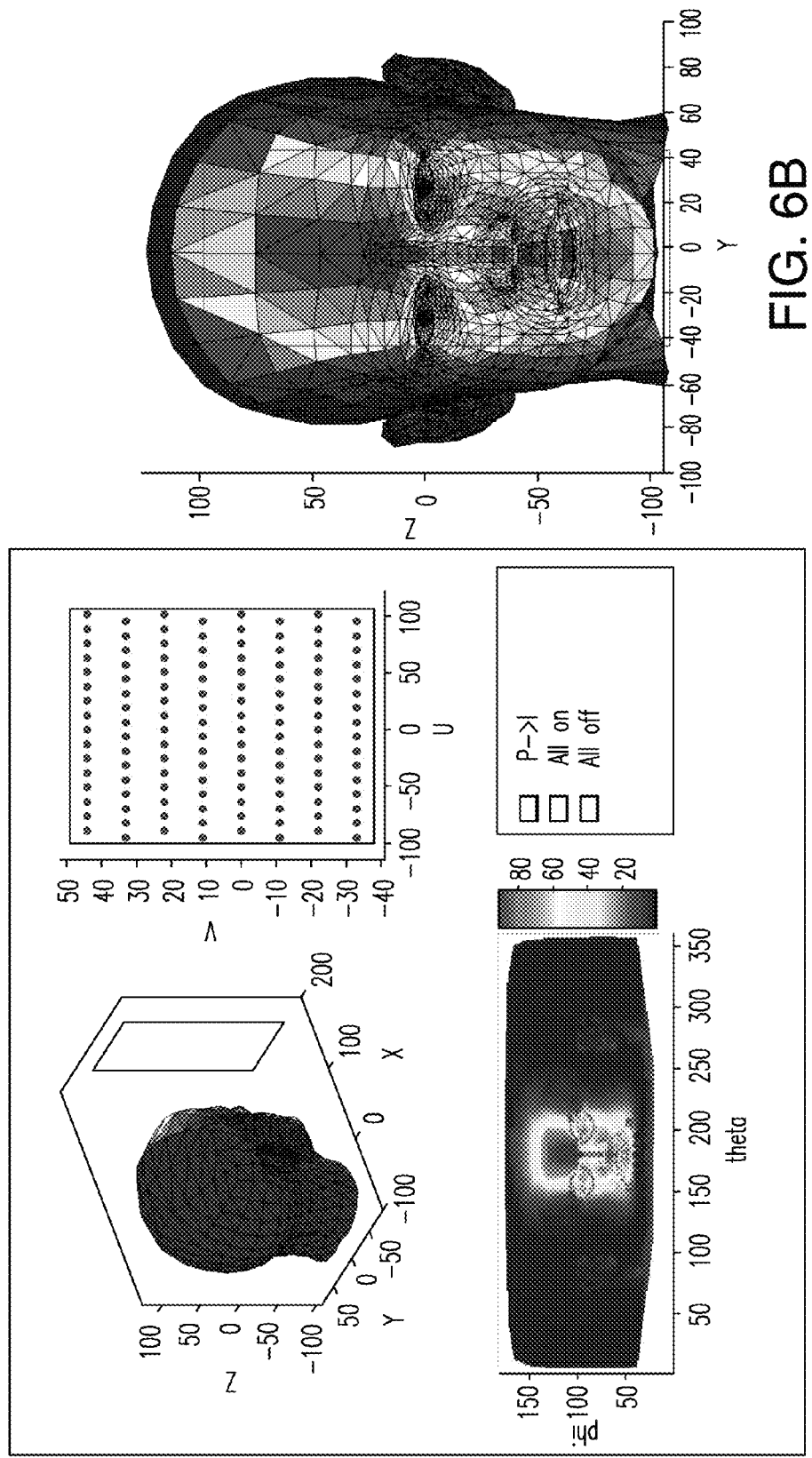
FIGS. 6A and 6B show the results of a 3D illumination modeling of a human's face illuminated with an Aktilite® 128 lamp, a photodynamic therapy lamp described in U.S. Patent Application Publication No. 2004/0260365, i.e. a photodynamic therapy lamp which is not one according to the invention.

As shown in FIG. 6, the model was used to calculate the illuminance of a patient's face/head from a lamp according to U.S. Patent Application Publication No. 2004/0260365, comprising a single lamp module which contains an array of 128 LEDs arranged in a regular honeycomb pattern of 16×8 LEDs, as displayed in the top right part of FIG. 6A. The lamp is sold under the name "Aktilite® 128" by Galderma. The lamp module is placed in front of the patient's face as shown in the top left part of FIG. 6A at a distance recommended by the supplier. The lower part of FIG. 6A shows the illuminance of the patient's face in a 2D picture while FIG. 6B shows the illuminance of the patient's face in a 3D model: only the middle part of the face from the nose/mouth outwards to the middle of the cheeks is illuminated by the lamp. The part from the outer corner of the eyes, from the middle of the cheeks outwards, the forehead and the ears are not or only poorly illuminated. As for the illuminated part, illumination is not homogeneous as apparent from the color distribution with a peak illumination of the middle of the forehead, the back of the nose, the chin and the inner corners of the eyes. Thus if this lamp were used for the photodynamic treatment of a patient's face, e.g. for the treatment of acne, efficacy of said treatment could not be ensured since parts of the face are not illuminated at all and other parts of the face are not homogeneously illuminated, i.e. different light doses are provided to different parts of the face.

Figure 7A:
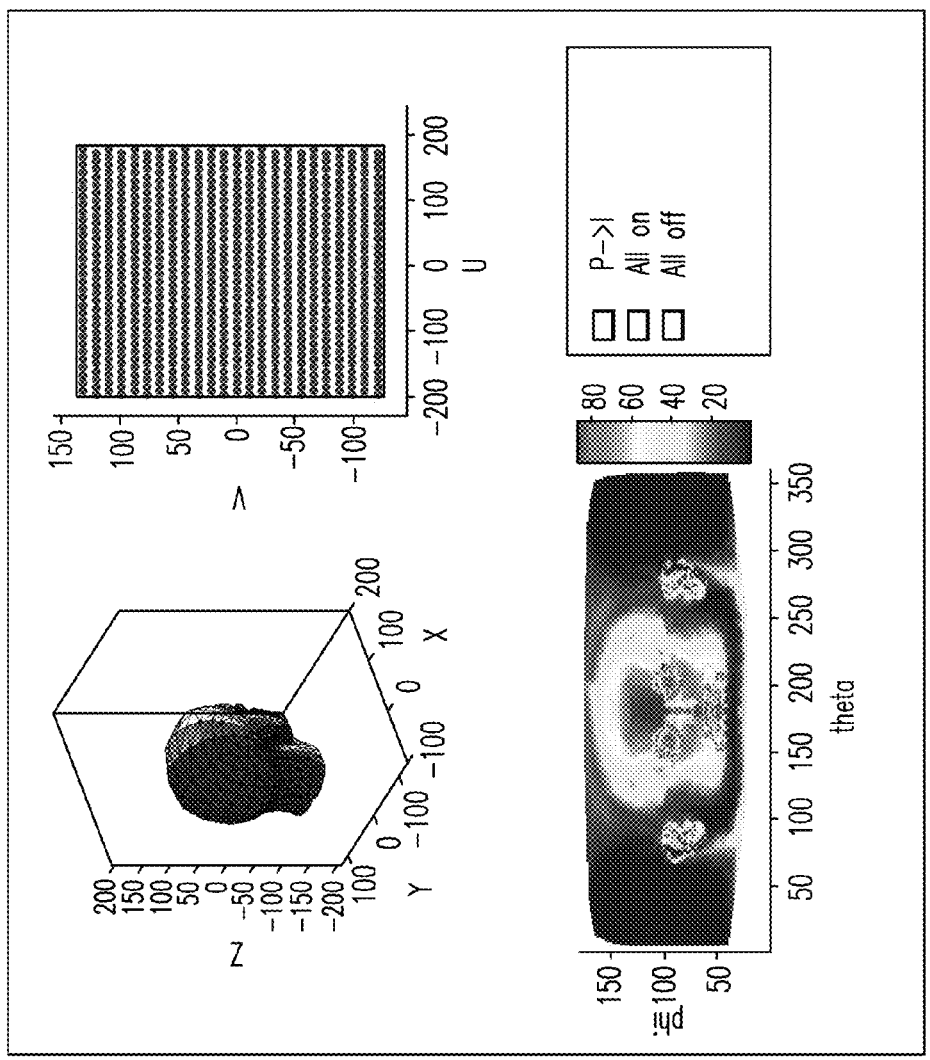
FIGS. 7A and 7B show the results of a 3D illumination modeling of a human's face illuminated with a photodynamic therapy lamp described in U.S. Patent Application Publication No. 2004/0260365, i.e. a photodynamic therapy lamp which is not one according to the invention.
Figure 7B:
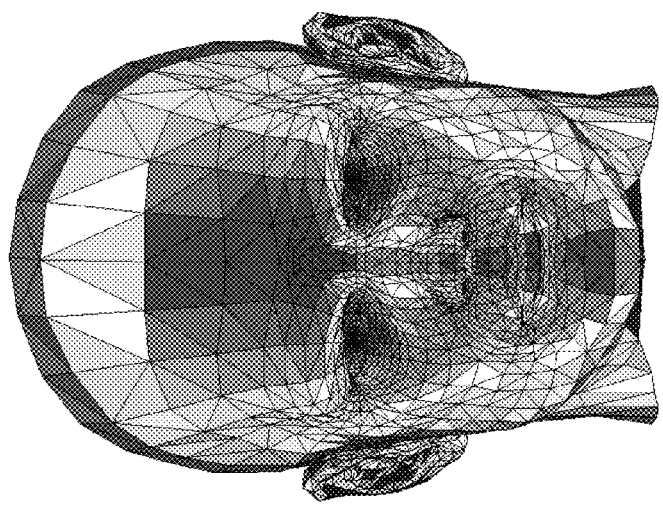

As shown in FIG. 7, the model was used to calculate the illuminance of a patient's face/head from a lamp according to U.S. Patent Application Publication No. 2004/0260365, comprising a single lamp module which contains an array of 768 LEDs arranged in a regular honeycomb pattern of 32×24 LEDs, as displayed in the top right part of FIG. 7A. Hence this lamp is an enlarged version of the Aktilite® 128 lamp used in FIG. 6, i.e. comprising a larger array of LEDs which are arranged in the same way as in the Aktilite® 128 lamp. The lamp module is placed in front of the patient's face as shown in the top left part of FIG. 7A at the same distance as in FIG. 6A. The lower part of FIG. 7A shows the illuminance of the patient's face in a 2D picture while FIG. 7B shows the illuminance of the patient's face in a 3D model: the whole face including the ears is illuminated by the lamp, however, as for the lamp in FIG. 6, illumination is not homogeneous as apparent from the color distribution with a peak illumination of the forehead, the back of the nose, the chin and the area under the eyes. Thus if this lamp were used for the photodynamic treatment of a patient's face, e.g. for the treatment of facial acne, efficacy of said treatment could not be ensured since the face is not homogeneously illuminated, i.e. different light doses are provided to different parts of the face.

Figure 8A:
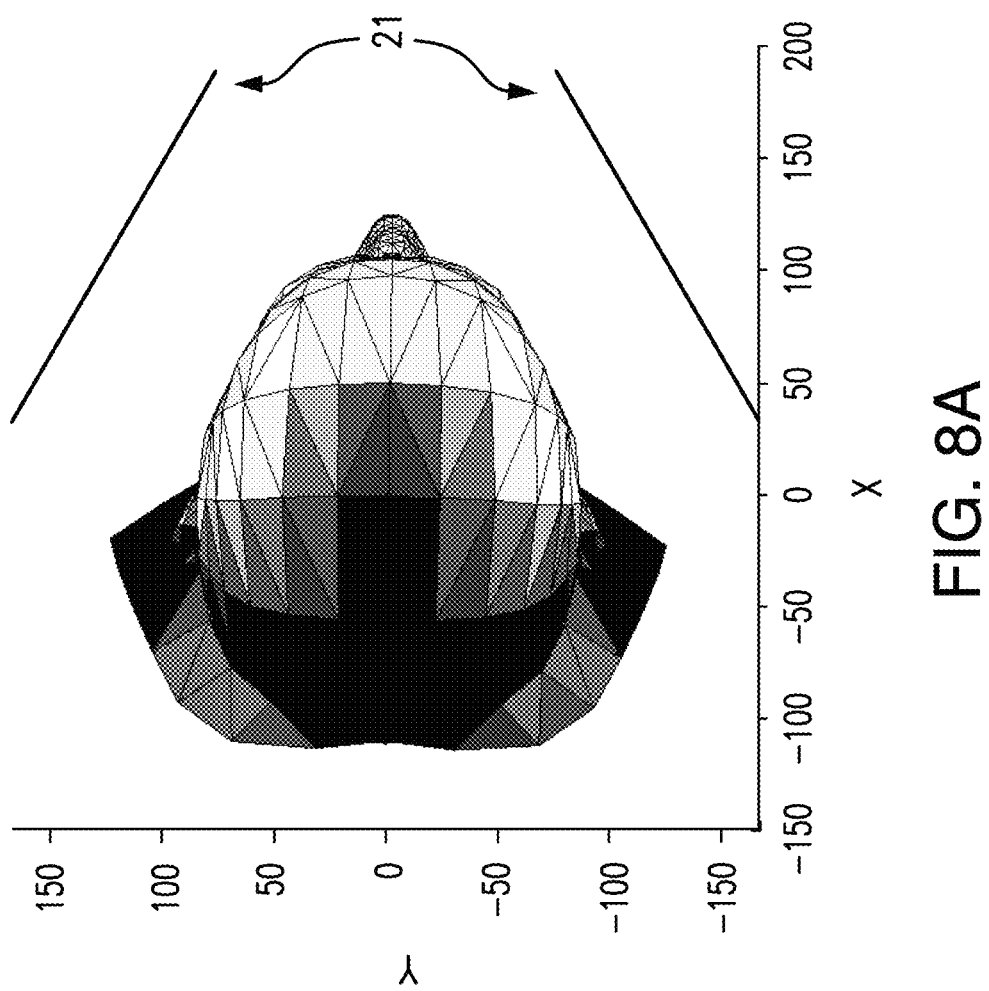
FIGS. 8A and 8B show the results of a 3D illumination modeling of a human's face illuminated with a photodynamic therapy lamp according to the invention wherein the lamp modules are positioned in the second position.
Figure 8B:
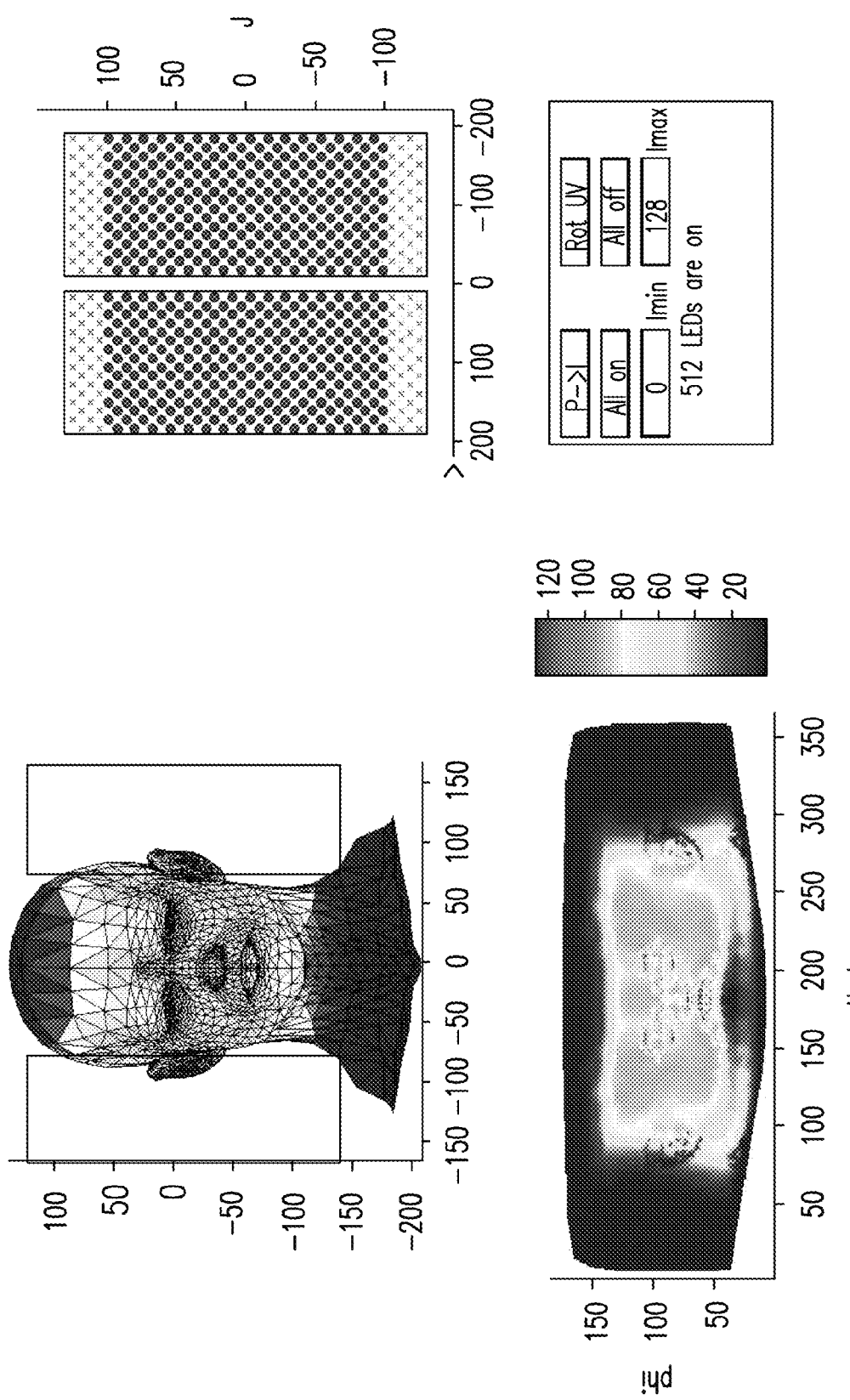

As shown in FIG. 8 the model was used to calculate the illuminance of a patient's face/head from a photodynamic therapy lamp 10 according to the invention comprising two lamp modules 21 and each lamp module comprising a two-dimensional array of 256 LEDs and a matching array of lenses. The LEDs in each lamp module are arranged in a regular honeycomb pattern of 16×16 LEDs as shown for the two lamp modules 21 in the top right of FIG. 8B. As illustrated in FIG. 8A in a view from above, the lamp modules 21 are positioned at a distance of 5-8 cm from the face in an angled orientation, i.e. second position with an angle of 60 degrees between them. The lower part of FIG. 8B shows the illuminance of the patient's face in a 2D picture while the upper left part of FIG. 8B shows the illuminance of the patient's face in a 3D model: the whole face is homogeneously illuminated by the lamp, i.e. no holes or hot-spots occur. The model was also used to assess the influence of head movement during treatment on the homogeneity of illumination and it was found that homogeneous illumination is still achieved with a 20 mm offset from the head's nominal position to the right, left, back and forward. Thus using the photodynamic therapy lamp according to the invention in a method of photodynamic treatment of a patient's face, e.g. for the treatment of facial acne, ensures efficacy and safety of said treatment since the face will be homogeneously illuminated, i.e. the correct light dose is provided to all parts of the face.

Whilst positioning the two lamp modules of the photodynamic therapy lamp according to the invention in the second position gives good overall head movement tolerance, the photodynamic therapy lamp according to the invention preferably provides a method to the operator to optimally align the patient's face/head and the two lamp modules in the second position, i.e. the angled orientation and to find the optimal distance of the patient's back or chest and the two lamp modules in the first position, i.e. the planar orientation. This will further ensure homogenous illumination of the treatment area and thus safety and efficacy of the treatment. For the alignment in the second position, two rows of LEDs of each array of LEDs are used to triangulate the position of the line of symmetry of the face/head to the lamp modules. The method enables centration, vertical and horizontal positioning in addition to setting the correct lamp module distance from the front of the face/head. Likewise, for the alignment in the first position two rows of LEDs of each array of LEDs are used to determine the optical vertical positioning, i.e. optimal distance from the lamp modules to the treatment surface. Further, a scale or other visual aid may be used to maintain a distance between the lamp modules and the treatment area between about 5 cm to 8 cm. Preferably, such scale or visual aid is provided on the lamp modules.

Figure 9A:
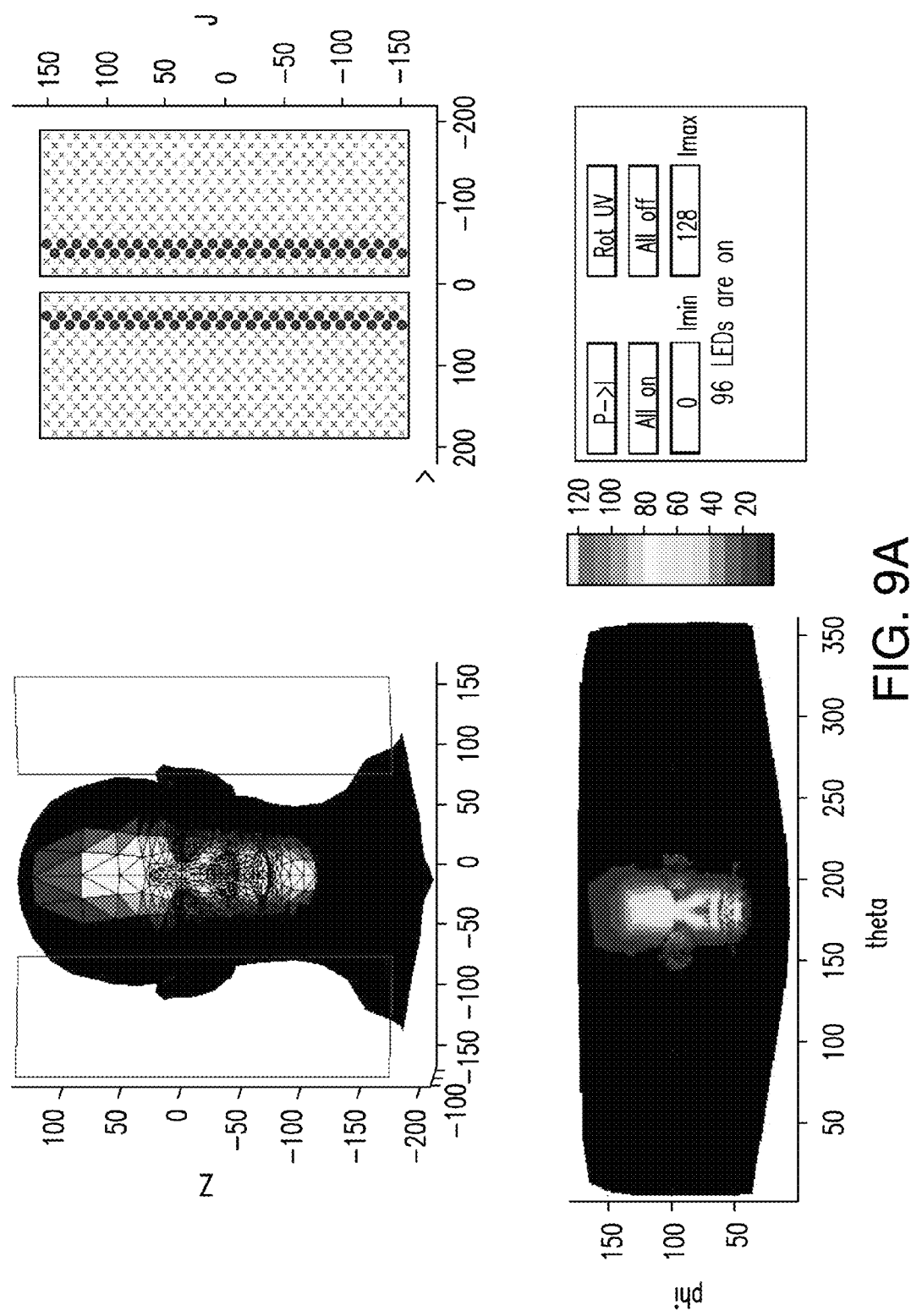
FIG. 9A shows the results of a 3D illumination modeling of a human's face illuminated by a two rows from each array of LEDs of a photodynamic therapy lamp according to the invention with the lamp modules in the second position, wherein the lamp is optimally positioned in relation to the human's face.
Figure 9B:
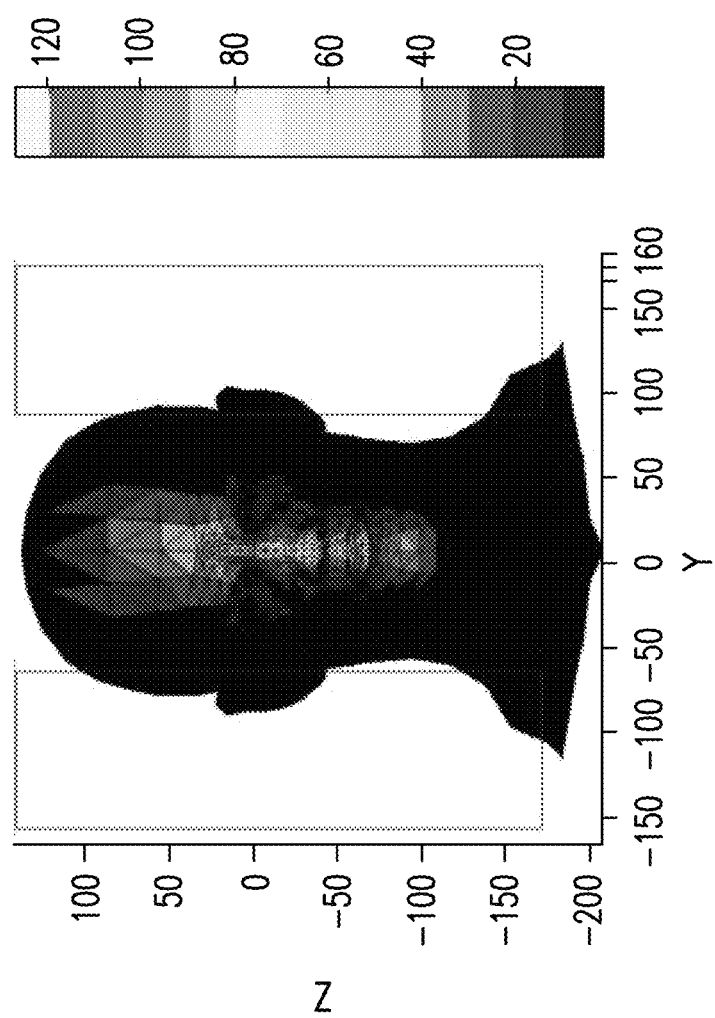

The lamp and mathematical model of FIG. 8 was used to calculate the illuminance of a patient's face/head as shown in FIG. 9. Only two rows of the two-dimensional array of 256 LEDs were used for the illumination as illustrated in the top right part of FIG. 9A. The lamp modules 21 and the patient's face/head are positioned as shown in FIG. 8A, i.e. the lamp modules 21 are positioned at a distance of 5 to 8 cm from the face in an angled orientation, i.e. second position, with an angle of 60 degrees between them. The lower part of FIG. 9A shows the illuminance of the patient's face in a 2D picture while the upper left part of FIG. 9A shows the illuminance of the patient's face in a 3D model: the line of symmetry of the face/head is homogeneously illuminated without a shadow in the center of the face and the peak illumination is aligned with said line of symmetry, indicating that the lamp is optimally positioned. If the lamp modules are positioned too far away from the patient's face, the offset from the optimal position is visible by reduced intensity (deep blue color) as illustrated in FIG. 9B. If the lamp modules are positioned too close to the patient's face, the offset from the optimal position is visible by a shadow in the center of the patient's face which extends from the forehead to the chin, as illustrated in FIG. 9C. If the lamp modules are positioned too far to the right (or the left) from the line of symmetry of the face/head this offset from the optimal position is visible by a peak illumination which is off said line of symmetry, i.e. which has moved to the right (or left) as illustrated in FIG. 9D. Thus when the photodynamic therapy lamp of the invention is used for the photodynamic treatment of the patient's face, the operator positions the lamp modules in the second position, i.e. angled orientation and places the lamp head with a distance of 5-8 cm from the patient's face in such way that the arrays of LEDs are oriented towards the patient's face (as shown in FIG. 3B). Then the operator simply has to run the alignment procedure (e.g. by pressing a button on the user interface and/or by selecting the alignment procedure from a menu) and, if there is a shadow visible on the patient's face, re-position the lamp head/lamp until there is no longer a shadow visible and the peak illumination is aligned with the line of symmetry of the patient's face.

The method of alignment of the lamp modules in the first position, i.e. planar orientation is based on the same principle and essentially carried out in the same way. Thus when the photodynamic therapy lamp of the invention is used for the photodynamic treatment of e.g. the patient's back or chest, the operator moves the lamp modules into the first position and positions the lamp head in a distance of 5-8 cm over a selected treatment area on the patient's back/chest with the arrays of LEDs facing the treatment area (as shown in FIGS. 2B and 2C). Then the operator simply has to run the alignment procedure (e.g. by pressing a button on the user interface and/or by selecting the alignment procedure from a menu) and, if there is a shadow visible on the patient's back/chest, re-position the lamp until there is an even illumination without a shadow.

Alternatively or in addition to the method of alignment, the lamp may provide a guide light feature, i.e. illumination from all LEDs with reduced intensity in the first or second position. With the guide light feature, the operator can check for correct position, e.g. even illumination of the face or back or chest by the lamp. Shadows indicate non- or poorly illuminated areas and the distance between the lamp and the treatment area can be adjusted in such a way that the shadows disappear.

The photodynamic lamp according to the invention is preferably used for the photodynamic treatment of the skin of a patient, preferably for the photodynamic treatment of contoured treatment areas like face and relatively flat treatment areas like the chest and the back. The photodynamic treatment may be a therapeutic treatment, i.e. a treatment to prevent, alleviate or cure a disease or disorder in a patient. Preferred examples of such therapeutic treatments are the treatment of dermatological diseases, i.e. diseases and disorders affecting the skin. Preferred examples of such dermatological diseases are acne, e.g. acne associated with bacteria such as *Propionibacterium* (e.g. *P. acnes, P. granulosum* and/or *P. avidum*), acne vulgaris, acne rosacea, acne conglobate, acne papulosa and premenstrual acne, psoriasis, skin cancers (e.g. Bowen's disease, squamous cell carcinoma) or pre-cancerous conditions of the skin such as actinic keratosis. The photodynamic treatment may be a cosmetic treatment, i.e. a treatment of ameliorate, alleviate or treat the signs of photoaging and to enhance the appearance of the skin. The photodynamic lamp according to the invention may be used in a photodynamic treatment without a photosensitizer (or a precursor of a photosensitizer). Such a treatment is also called "phototherapy" or "light therapy" and may be a therapeutic treatment, i.e. a treatment to prevent, alleviate or cure a disease or disorder in a patient or a cosmetic treatment. Alternatively, the photodynamic lamp according to the invention may be used in a photodynamic treatment with a photosensitizer (or a precursor of a photosensitizer). In general, any known photosensitizers or precursors thereof can be used in a method of PDT wherein the photodynamic therapy lamp according the invention is used.

Typical such photosensitizers include dyes like hypericin and PVP hypericin, psoralens, porphyrins such as hematoporphyrins, protoporphyrins, uroporphyrins, coproporphyrins, benzoporphyrins or deuteroporphyrins, in particular Photofrin® (profimer sodium), photosan III or verteporfin; chlorins, including bacteriochlorins and isochlorins such as chlorine e6, talaporfin or temoporfin and phthalocyanines such as aluminum- and silicon phthalocyanines Preferably, precursors of photosensitizers are used in a method of PDT wherein the photodynamic therapy lamp according to the invention is used. Typical precursors of photosensitizers include 5-aminolevulinic acid (5-ALA) and certain derivatives thereof, e.g. 5-ALA N-derivatives or 5-ALA esters or salts thereof, preferably derivatives and salts thereof as described in WO 96/28412, WO 99/53962, U.S. Patent Application Publication No. 2005/124984, U.S. Patent Application Publication No. 2008/0064752 and U.S. Patent Application Publication No. 2010/0273725.

Photosensitizers or precursors of photosensitizers are formulated with compatible excipients that are known in the art as described for instance in WO 96/28412, WO 99/53962, U.S. Patent Application Publication No. 2011/0020441, U.S. Patent Application Publication No. 2011/0293528, U.S. Patent Application Publication No. 2012/0134921, U.S. Patent Application Publication No. 2012/0136055, U.S. Patent Application Publication No. 2011/0212146, WO 2011/161220, and WO 2012/004399. For parenteral administration the photosensitizer or precursor of photosensitizer can be formulated as a solution, preferably aqueous solution. For enteral administration, the photosensitizer or precursor of photosensitizer can be formulated as a solid for oral administration, e.g. a pill, tablet, powder, granulate or alternatively, the photosensitizer or precursor of photosensitizer can be formulated as a semi-solid for oral administration, e.g. a gel, emulsion, foam or ointment. Further, the photosensitizer or precursor of photosensitizer can be formulated as a liquid for oral administration, e.g. a solution, suspension or syrup. For topical administration, e.g. for application to the skin, the photosensitizer or precursor of photosensitizer can be formulated as a liquid, e.g. a solution such as an aqueous and/or alcoholic solution or suspension, as a semi-solid, e.g. a cream, emulsion, lotion, ointment, gel, foam and paste or as a solid, e.g. a transdermal patch. For the photodynamic treatment of acne, actinic keratosis or for cosmetic treatment, the photosensitizer or precursor of photosensitizers are preferably formulated for topical application to the skin, more preferably as a semi-solid, e.g. a cream, emulsion, lotion, ointment, gel, foam and paste or as a solid, e.g. a transdermal patch.

If the photodynamic lamp according to the invention is used in the treatment of acne, it is preferably used with a precursor of a photosensitizer, more preferably with 5-ALA or a salt thereof or a derivative of 5-ALA or a salt thereof, most preferably with a 5-ALA ester or a salt thereof, e.g. as described in U.S. Patent Application Publication No. 2008/0188558 and U.S. Patent Application Publication No. 2010/0137439. In a preferred embodiment, the photodynamic lamp according to the invention is used in the treatment of acne with 5-ALA methyl ester or a salt thereof, preferably with the hydrochloride salt of 5-ALA methyl ester.

If the photodynamic lamp according to the invention is used in the treatment of actinic keratosis it is preferably used with a precursor of a photosensitizer, more preferably with 5-ALA or a salt thereof or a derivative of 5-ALA or a salt thereof, most preferably with a 5-ALA ester or a salt thereof, e.g. as described in U.S. Patent Application Publication No. 2010/0137439. In a preferred embodiment, the photodynamic lamp according to the invention is used in the treatment of actinic keratosis with 5-ALA methyl ester or a salt thereof, preferably with the hydrochloride salt of 5-ALA methyl ester.

If the photodynamic lamp according to the invention is used in the cosmetic treatment of photoaged skin, it is preferably used with a precursor of a photosensitizer, more preferably with 5-ALA or a salt thereof or a derivative of 5-ALA or a salt thereof, most preferably with a 5-ALA ester or a salt thereof, e.g. as described in U.S. Patent Application Publication No. 2011/0212146. In a preferred embodiment, the photodynamic lamp according to the invention is used in the cosmetic treatment of photoaged skin with 5-ALA hexyl ester or a salt thereof, preferably with the hydrochloride salt or the napsylate salt of 5-ALA hexyl ester.

The concentration of the photosensitizers or precursors of photosensitizers in a pharmaceutical or cosmetic composition for use in a method of PDT with the photodynamic lamp according to the invention procedures depends upon the nature of the photosensitizer or precursor of photosensitizer, the nature of the composition/formulation, the mode of administration, the disease, disorder or condition to be treated and may be varied or adjusted according to choice. For precursors of photosensitizers, such as 5-ALA and derivatives of 5-ALA, generally, concentration ranges of 0.01 to 50% by weight, such as 0.05 to 20% by weight, or 1 to 10% by weight, e.g. 1 to 5% by weight, are suitable.

For the photodynamic therapeutic treatment of acne, if a 5-ALA ester or salt thereof is used as a precursor of a photosensitizer, the concentration of such 5-ALA esters or salts thereof in a pharmaceutical composition for topical administration to the skin is preferably 1 to 20% by weight, more preferably 5 to 16% by weight, even more preferably 6 to 10% by weight and most preferably 7 to 9% by weight.

For the photodynamic therapeutic treatment of actinic keratosis, if a 5-ALA ester or salt thereof is used as a precursor of a photosensitizer, the concentration of such 5-ALA esters or salts thereof in a pharmaceutical composition for topical administration to the skin is preferably 1 to 20% by weight, more preferably 5 to 16% by weight.

For the photodynamic cosmetic treatment of photoaged skin, if a 5-ALA ester or salt thereof is used as a precursor of a photosensitizer, the concentration of such 5-ALA esters or salts thereof in a cosmetic composition for topical administration to the skin is preferably 2% or less by weight, more preferably 0.02 to 1.75% by weight, even more preferably 0.05 to 1.5% by weight and most preferably 0.1 to 1% by weight.

Figure 10:
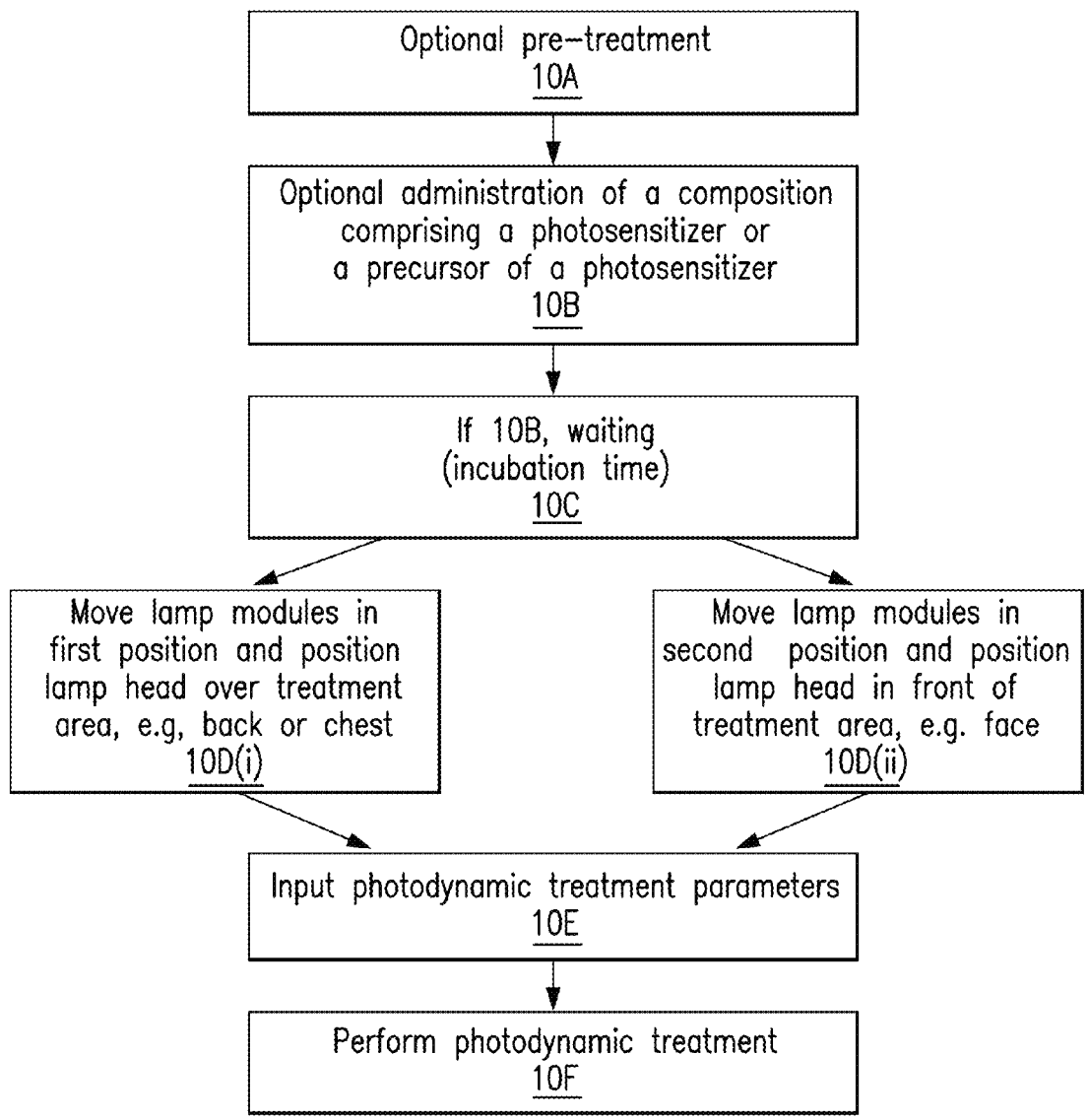
FIG. 10 schematically illustrates a method of using the photodynamic therapy lamp according to the invention in a photodynamic treatment.

FIG. 10 illustrates a method of using the lamp in photodynamic treatment according to an exemplary embodiment of the present invention.

At step 10A, the PDT procedure may optionally start with a pre-treatment of the treatment area, e.g. the skin to be treated. Such a pre-treatment may comprise the step of cleansing the skin with a suitable cleansing agent such as soap/water. Further, such pre-treatment may comprise the step of removing dead skin cells on the skin surface, e.g. with keratolytic agents, such as agents comprising urea and/or hydroxy acids such as salicylic acid or lactic acid or by manually scrubbing away such dead cells, e.g. with a brush. Pre-treatment may also comprise the step of preparing the surface of a lesion, e.g. an actinic keratosis lesion, with a dermal curette to remove scales and crusts and to roughen the surface of the lesion.

If the photodynamic lamp according to the invention is used with a photosensitizer or precursor of a photosensitizer, a pharmaceutical or cosmetic composition comprising such photosensitizer or precursor of a photosensitizer is administered to the patient at step 10B. Alternatively, the photodynamic lamp according to the invention is used without a photosensitizer or precursor of photosensitizer. The mode of administration is dependent on the composition and nature of the photosensitizer or precursor of photosensitizer. Typically, administration can be done parenterally (infusion, injection), enterally (e.g. oral or rectal administration) or topically.

The waiting step 10C is carried out to achieve an effective concentration of photosensitizer in the target cells of the treatment area (incubation time) or to convert the precursor into a photosensitizer and achieve effective concentration of the photosensitizer in the target cells of the treatment area, in case a precursor is used. The incubation time is dependent on the nature of the photosensitizer or precursor of photosensitizer, its concentration, its formulation and also its mode of administration. In general, incubation time ranges from 0 minutes to several hours, e.g. 12 hours. For topical administration to skin, the incubation time is 5 min to 4 hours, more preferably 15 min to 3 hours, even more preferably 30 min to 2 hours and most preferably 1 to 1.5 hours. For topical administration to the skin, the incubation can be carried out under occlusion, e.g. with an adhesive occlusive dressing such as Tegaderm® or Opsite®. Such occlusive dressings may enhance the penetration and absorption of a topically-administered formulation. After the incubation, the remainder of the composition comprising the photosensitizer or precursor of photosensitizer may be removed, if the composition was topically administered.

At step 10D(i) of FIG. 10 for photodynamic treatment of a relatively flat treatment surface on a patient, e.g. the patient's chest or back, the lamp modules 21 are placed in the planar orientation, i.e. the first position, e.g. by rotating the lamp modules 21 away from each other until the lamp modules 21 are in the correct first position, preferably locked in said first position by means of locking elements. Then, the lamp head 20 is positioned at a distance suitable to homogeneously illuminate said relatively flat treatment surface, e.g. by using the alignment method described hereinbefore.

At step 10D(ii) for photodynamic treatment of a contoured treatment surface on a patient, e.g. the patient's face, the lamp modules 21 are placed in the angled orientation, i.e. second position, e.g. by rotating the lamp modules 21 towards each other until the lamp modules 21 are in the correct second position, preferably locked in said second position by means of locking elements. Then, the lamp head 20 is positioned at a distance suitable to homogeneously illuminate said contoured treatment surface, e.g. by using the alignment method described with reference to FIG. 9.

For facial treatments, it is recommended that the patient wears protective eye shields, and for other treatments, it is recommended that the patient wears ordinary protective glasses. For all treatments, it is recommended that the operator wears professional protective glasses or goggles.

After the lamp head 20 is correctly positioned for treatment, the photodynamic treatment parameters, e.g. required light dose and/or the illumination time for the LEDs of the lamp modules 21 are input by the operator using the user interface on the lamp 10 at step 10E.

Then, at step 10F, the photodynamic treatment is performed at the required light dose and illumination time. During treatment, the user interface may display or otherwise indicate the treatment parameters and remaining treatment time. In a preferred embodiment, the treatment may be (repeatedly) interrupted by the operator, e.g. if the patient experiences pain. The treatment can then be continued at any time within a certain period (e.g. an hour) and the lamp delivers the remaining light dose. At the completion of treatment, the user interface may display or otherwise indicate such completion by visual and/or audio output. The photodynamic treatment can be paused, restarted, and/or interrupted as necessary in order to provide appropriate treatment to the patient. Further, the patient may use the optional patient cooling unit as desired throughout the treatment.

The following examples illustrate the use of the photodynamic therapeutic lamp according to the invention in methods of photodynamic therapy:

EXAMPLE 1

Photodynamic Treatment of Acne

The objective of the clinical study was to investigate the efficacy and safety of a cream comprising 10% by weight 5-ALA methyl ester hydrochloride salt (corresponding to 8% by weight 5-ALA methyl ester)(also referred to in the following examples as "Visonac® cream" (a registered trademark of Photocure ASA)) vs. placebo (the cream formulation without 5-ALA methyl ester hydrochloride) followed by red light illumination carried out with a lamp according to the invention (i.e., a photodynamic therapy lamp 10 as shown and described with reference to FIGS. 1 to 5)(also referred to in the following examples as "Nedax® lamp" (a registered trademark of Photocure ASA)) in severe acne patients. The clinical study was a multicenter, randomized, double-blind and placebo controlled study. A total of 153 male and female patients aged 12 to 35 years were enrolled at 15 sites in the United States of America having Fitzpatrick skin type I-VI, 25 to 75 inflammatory acne lesions and 20 to 100 non-inflammatory acne lesions, no more than 3 nodules and an Investigator's Global Assessment (IGA) score of 4. Visonac® cream or placebo was administered to the skin and left to incubate under occlusion (Opsite®, Smith and Nephew) for 1.5 hours. Illumination was carried out with the Nedax® lamp comprising two lamp modules 21 comprising each a two-dimensional array of 256 LEDs which provide red light at an average wavelength of 632 nm and a matching array of lenses. The two lamp modules 21 were positioned in a planar orientation, i.e. first position for the treatment of the back or chest at an angle of 168.5 degree and in an angled orientation, i.e. second position for the treatment of the face at an angle of 60 degree. The lamp modules 21 were positioned at a distance of 5-8 cm from the treatment area. The lamp was set to an irradiance (fluence rate) of 68 mW/cm$^2$ and a light dose of 37 J/cm$^2$ was provided. The patients could use the patient cooling unit of the lamp to provide cooling to the treated areas as desired and possible throughout the treatment. The patients wore protective goggles during the treatment All patients received 4 treatments 2 weeks apart (at week 0, 2, 4 and 6). The primary end-point of the study was reduction of inflammatory lesions 6 weeks after the last treatment (week 12). Secondary end-points were proportion of patients with success according to IGA (success defined as an improvement of at least 2 grades from the baseline), reduction in non-inflammatory lesions, pain experienced during illumination using a Visual Analogue Scale (VAS) from 0 to 10 and erythema score. Patients treated with Visonac® cream in combination with the Nedax® lamp had a statistically significant reduction in inflammatory lesions of 43.8% as compared to 26.6% in the placebo group (p=0.003). Visonac® cream treatment showed a statistically significant higher IGA treatment success rate compared to placebo, 44.0% versus 26.4% (p=0.013). A comparable reduction in non-inflammatory lesions was achieved in both groups (p=0.853). Post treatment erythema was reported more frequently in the Visonac® cream group (89% versus 70%), which generally subsided by the following day. Twelve patients withdrew from the study due to adverse events. Six (6%) patients in the Visonac® cream group withdrew due to pain related adverse events (pain, burning or stinging). No serious adverse events were reported in the study.

In conclusion, photodynamic treatment of acne with Visonac® cream and Nedax® lamp, i.e., a photodynamic therapy lamp 10 according to the invention, significantly decreased the number of inflammatory lesions and significantly improved IGA success rate compared to placebo. The treatment was well tolerated. Comparable efficacy was demonstrated in reducing non-inflammatory lesions.

EXAMPLE 2

Photodynamic Treatment of Actinic Keratosis

Actinic keratosis patients having multiple or few but fairly extensive lesions on the face are treated using a cream comprising 20% by weight 5-ALA methyl ester hydrochloride salt (corresponding to 16% by weight 5-ALA methyl ester), e.g. Metvixia® cream (Galderma), followed by red light illumination which is carried out with a Nedax® lamp, i.e., a photodynamic therapy lamp 10 according to the invention. The surface of the lesions is prepared with a small dermal curette to remove scales and crusts and to roughen the surface of the lesions. The cream is administered to the lesions and left to incubate under occlusion for 3 hours. The remainder of the cream is removed and illumination is carried out with the Nedax® lamp comprising two lamp modules 21 comprising each a two-dimensional array of 256 LEDs which provide red light at an average wavelength of 632 nm and a matching array of lenses. The two lamp modules 21 of the lamp are positioned in an angled orientation, i.e. second position for the treatment of the face at an angle of 60 degree. The lamp modules 21 are positioned at a distance of 5-8 cm from the face. The lamp is set to an irradiance (fluence rate) of 68 mW/cm² and a light dose of 37 J/cm² is provided. The patients may use the patient cooling unit of the lamp 10 to provide cooling to the face as desired throughout the treatment. The patients wear protective goggles during the treatment

EXAMPLE 3

Photodynamic Treatment of Actinic Keratosis

Actinic keratosis patients having multiple or few but fairly extensive lesions on the face are treated using essentially anhydrous 5-ALA hydrochloride which is admixed with a liquid diluents just prior to its use to result in a 20% solution for topical administration to the skin (e.g. Levulan® Kerastick®, Dusa Pharmaceuticals) followed by blue light illumination which is carried out with a photodynamic therapy lamp 10 according to the invention. The surface of the lesions is prepared with a small dermal curette to remove scales and crusts and to roughen the surface of the lesions. The solution is administered to the lesions. After the initially administered solution has dried, one or more subsequent administrations may be carried out to approximately administer 2 mg/cm² of 5-ALA hydrochloride. Formation of photosensitive porphyrin in the cells of the treated lesions occurs over the next 14-18 hours, during which time exposure to direct sunlight or other bright light sources should be minimized. Between 14 and 18 hours after administration of the ALA, illumination is carried out with a photodynamic therapy lamp according to the invention comprising two lamp modules comprising each a two-dimensional array of 256 LEDs which provide blue light at an average wavelength of 417 nm and a matching array of lenses. The two lamp modules of the lamp are positioned in an angled orientation, i.e. second position for the treatment of the face at an angle of 60 degree. The lamp modules are positioned at a distance of 5-8 cm from the face. A light dose of 10 J/cm² is provided. The patients may use the patient cooling unit of the lamp to provide cooling to the face as desired throughout the treatment. The patients wear protective goggles during the treatment

EXAMPLE 4

Cosmetic Photodynamic Treatment of Photoaged Skin

Patients whose faces show typical signs of photoaging such as roughness, sallowness, mottled pigmentation, diffuse facial redness, telangiectasis and/or the formation of fine lines or wrinkles are treated using a cream comprising 0.5% by weight 5-ALA hexyl ester napsylate or 0.5% by weight 5-ALA hexyl ester hydrochloride (e.g. Allumera® cream, Photocure Inc.), followed by red light illumination which is carried out with a Nedax® lamp, i.e., a photodynamic therapy lamp 10 according to the invention. The face is cleaned with soap/water and gently dried. About 2 g of the cream is administered to all areas of the face except the areas which are covered by goggles during illumination. The cream is left on the face for about 1 hour, and the remainder of the cream is removed. Illumination is carried out with the Nedax® lamp comprising two lamp modules 21 comprising each a two-dimensional array of 256 LEDs which provide red light at an average wavelength of 632 nm and a matching array of lenses. The two lamp modules 21 of the lamp are positioned in an angled orientation, i.e. second position for the treatment of the face at an angle of 60 degree. The lamp modules 21 are positioned at a distance of 5-8 cm from the face. The lamp is set to an irradiance (fluence rate) of 68 mW/cm² and a light dose of 37 J/cm² is provided. The patients may use the patient cooling unit of the lamp 10 to provide cooling to the face as desired throughout the treatment. The patients wear protective goggles during the treatment.

EXAMPLE 5

Photodynamic Treatment of Acne

Patients suffering from non-inflammatory acne (i.e. the majority of acne lesions are non-inflammatory lesions) or moderate inflammatory acne on their faces, backs and/or chest are treated by red light illumination carried out with a Nedax® lamp (i.e., a photodynamic therapy lamp 10 according to the invention) without the use of a photosensitizer or precursor of a photosensitizer. Illumination is carried out with the Nedax® lamp comprising two lamp modules 21 comprising each a two-dimensional array of 256 LEDs which provide red light at an average wavelength of 632 nm and a matching array of lenses. The two lamp modules 21 are positioned in a planar orientation, i.e. first position for the treatment of the back or chest at an angle of 168.5 degree and in an angled orientation, i.e. second position for the treatment of the face at an angle of 60 degree. The lamp modules 21 are positioned at a distance of 5-8 cm from the treatment area. The lamp is set to an irradiance (fluence rate) of 68 mW/cm² and a light dose of 37 J/cm² is provided. The patients may use the patient cooling unit of the lamp to provide cooling to the treated areas as desired and possible throughout the treatment. The patients wear protective goggles during the treatment. Such a treatment can be a primary treatment, an alternative to pharmaceuticals or topical, or an adjunct to skin care programs.

EXAMPLE 6

Photodynamic Treatment of Acne

Patients suffering from moderate inflammatory acne on their faces, backs and/or chest are treated by blue light illumination carried out with a photodynamic therapy lamp according to the invention without the use of a photosensitizer or precursor of a photosensitizer. Illumination is carried out with a lamp comprising two lamp modules comprising each a two-dimensional array of 256 LEDs which provide blue light at an average wavelength of 417 nm and a matching array of lenses. The two lamp modules are positioned in a planar orientation, i.e. first position for the treatment of the back or chest at an angle of 168.5 degree and in an angled orientation, i.e. second position for the treatment of the face at an angle of 60 degree. The lamp modules are positioned at a distance of 5-8 cm from the treatment area. A light dose of 10 J/cm² is provided. The patients may use the patient cooling unit of the lamp to provide cooling to the treated areas as desired and possible throughout the treatment. The patients wear protective goggles during the treatment. The treatment may be carried out about once or twice per week and may go on for about 5 weeks or so. Such a treatment can be a primary treatment, an alternative to pharmaceuticals or topical, or an adjunct to skin care programs.

The foregoing description discloses only non-limiting embodiments of the present invention. Modification of the above-disclosed exemplary dual panel photodynamic therapy lamp, and a method of using the same, which fall within the scope of the invention, will be readily apparent to those of ordinary skill in the art.

Accordingly, while the present invention has been disclosed in connection with the above non-limiting embodiments, it should be understood that other embodiments may fall within the spirit and scope of the invention, as defined by the following claims.

The invention claimed is:

1. A method of photodynamic treatment of acne comprising
   (i) administering a composition comprising a 5-ALA ester, or a salt thereof, to a treatment area, which is an area affected by acne on a patient;
   (ii) exposing the treatment area to light from a photodynamic therapy lamp following a waiting period;
   wherein the photodynamic therapy lamp comprises two lamp modules and each of the lamp module comprises a two-dimensional array of LEDs and the lamp modules are configured to be movable only between a first position and a second position, wherein in the first position the two lamp modules are oriented such that there is an angle of 157 to 180 degrees between the lamp modules, and in the second position the angle between the lamp modules is from 55 degrees to 65 degrees;
   wherein the lamp modules are positioned at 5 to 8 cm from the treatment area and are positioned in the first position if the treatment area is a flat treatment area and are positioned in the second position if the treatment area is a contoured treatment area.

2. The method according to claim 1, further comprising inputting parameters of the photodynamic treatment via a user interface and performing the photodynamic treatment based on the inputted parameters.

3. The method according to claim 2, wherein the parameters include an irradiance of 68 mW/cm$^2$.

4. The method according to claim 2, wherein the parameters include a light dose of 37 J/cm$^2$.

5. The method according to claim 2, wherein the composition is a cream, the waiting period is 1.5 hours, the treatment area is occluded during the waiting period, the lamp modules are positioned in the second position, the angle in the second position is 60 degrees and the treatment area is a face or the lamp modules are positioned in the first position, the angle in the first position is 168.5 degrees and the treatment area is a chest or a back, the parameters include a light dose of 37 J/cm$^2$ and wherein the treatment area is exposed to light at a nominal wavelength of 632±5 nm.

6. The method according to claim 5, wherein the photodynamic treatment is carried out in the form of 4 treatments 2 weeks apart.

7. The method according to claim 5, wherein the composition comprises 5-ALA methyl ester.

8. The method according to claim 7, wherein the 5-ALA methyl ester is a hydrochloride salt.

9. The method according to claim 5, wherein the composition comprises 5-ALA methyl ester hydrochloride salt at a concentration of 10% by weight.

10. The method according to claim 9, wherein the photodynamic treatment is carried out in the form of 4 treatments 2 weeks apart.

11. The method according to claim 1, wherein the 5-ALA ester is a 5-ALA methyl ester.

12. The method according to claim 11, wherein the 5-ALA methyl ester is a hydrochloride salt.

13. The method according to claim 1, wherein the composition comprises a 5-ALA ester or a salt thereof in a concentration of 6 to 10% by weight.

14. The method according to claim 1, wherein the composition comprises 5-ALA methyl ester hydrochloride salt at a concentration of 10% by weight.

15. The method according to claim 1, wherein the waiting period is from 1 to 3 hours.

16. The method according to claim 15, wherein the waiting period is 1.5 hours.

17. The method according to claim 1, wherein the treatment area is occluded during the waiting period.

18. The method according to claim 1, wherein the contoured treatment area is a face.

19. The method according to claim 1, wherein the lamp modules are positioned in the second position, the angle in the second position is 60 degrees, and the treatment area is a face.

20. The method according to claim 1, wherein the flat treatment area is a chest or a back.

21. The method according to claim 1, wherein the lamp modules are positioned in the first position, the angle in the first position is from 157 to 180 degrees, and the treatment area is a chest or a back.

22. The method according to claim 21, wherein the angle is 168.5 degrees.

23. The method according to claim 1, further comprising aligning the lamp modules with the treatment area.

24. The method according to claim 1, wherein the treatment area is exposed to light at a nominal wavelength of 632±5 nm.

25. The method according to claim 1, wherein the photodynamic treatment is carried out in the form of 4 treatments 2 weeks apart.

* * * * *